United States Patent
Schoenfisch et al.

(10) Patent No.: US 11,324,773 B2
(45) Date of Patent: *May 10, 2022

(54) COMPOUNDS, COMPOSITIONS AND METHODS FOR INHIBITING A PATHOGEN AND/OR MODIFYING MUCUS

(71) Applicant: The University of North Carolina at Chapel Hill, Chapel Hill, NC (US)

(72) Inventors: Mark H. Schoenfisch, Chapel Hill, NC (US); Katelyn Reighard, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/500,755

(22) PCT Filed: Apr. 10, 2018

(86) PCT No.: PCT/IB2018/052522
§ 371 (c)(1),
(2) Date: Oct. 3, 2019

(87) PCT Pub. No.: WO2018/189687
PCT Pub. Date: Oct. 18, 2018

(65) Prior Publication Data
US 2020/0085858 A1 Mar. 19, 2020

Related U.S. Application Data

(60) Provisional application No. 62/483,655, filed on Apr. 10, 2017.

(51) Int. Cl.
*A61K 31/785* (2006.01)
*A61P 31/04* (2006.01)
*A61K 9/00* (2006.01)

(52) U.S. Cl.
CPC .......... *A61K 31/785* (2013.01); *A61K 9/0065* (2013.01); *A61P 31/04* (2018.01)

(58) Field of Classification Search
CPC .. C08B 37/003; A61K 9/0065; A61K 9/0073; A61K 31/722; A61K 31/785; A61K 47/58; A61K 47/60; A61K 47/61
See application file for complete search history.

(56) References Cited

U.S. PATENT DOCUMENTS

| | | | |
|---|---|---|---|
| 5,234,933 | A | 8/1993 | Marnett et al. |
| 5,326,902 | A | 7/1994 | Seipp et al. |
| 5,859,058 | A | 1/1999 | Zimmerman et al. |
| 6,180,082 | B1 | 1/2001 | Woltering et al. |
| 6,451,337 | B1 | 9/2002 | Smith et al. |
| 9,850,322 | B2 | 12/2017 | Schoenfisch et al. |
| 10,759,877 | B2 | 9/2020 | Schoenfisch et al. |
| 2015/0225488 | A1* | 8/2015 | Schoenfisch ............ A61P 15/00 514/55 |
| 2016/0158169 | A1 | 6/2016 | O'Neil et al. |

FOREIGN PATENT DOCUMENTS

| | | | |
|---|---|---|---|
| EP | 1004294 A1 | 5/2000 | |
| WO | WO 93/25521 A1 | 12/1993 | |
| WO | WO-2005110052 A2 * | 11/2005 | .......... A61M 16/024 |
| WO | WO 2009/049208 A1 | 4/2009 | |

OTHER PUBLICATIONS

Charrier, C. et al "Cysteamine (Lynovex), a novel mucoactive antimicrobial & antibiofilm agent . . . " Orphanet J. Rare Dis., vol. 9, pp. 1-11. (Year: 2014).*
WIPO Application No. PCT/IB2018/052522, PCT International Search Report and Written Opinion of the International Searching Authority dated Jun. 27, 2018.
Reighard et al., "Disruption and eradication of P. aeruginosa biofilms using nitric oxide-releasing chitosan oligosaccharides," Biofouling, 31:775-787, (2015).
European Application No. 18784598.7, Extended European Search Report dated Jan. 13, 2021.
Albina, Jorge E. and Jonathan S. Reichner, "Role of nitric oxide in mediation of macrophage cytotoxicity and apoptosis," Cancer and Metastasis Reviews, 17:39-53, (1998).
Anderson et al., "The Relationship of Mucus Concentration (Hydration) to Mucus Osmotic Pressure and Transport in Chronic Bronchitis," American journal of respiratory and critical care medicine, 192(2):182-190, (Jul. 2015).
Burney et al., "The chemistry of DNA damage from nitric oxide and peroxynitrite," Mutation Research/Fundamental and Molecular Mechanisms of Mutagenesis, 424:37-49, (1999).
Carpenter et al., "Influence of Scaffold Size on Bactericidal Activity of Nitric Oxide Releasing Silica Nanoparticles," ACS Nano, 5(9):7235-7244, (Sep. 2011).
Carpenter et al., "Dual action antimicrobials: nitric oxide release from quaternary ammonium-functionalized silica nanoparticles," Biomacromolecules, 13(10):3334-3342, (2012).
Carpenter et al., "Nitric oxide release: Part II. Therapeutic applications," Chem. Soc. Rev., 41(10):3742-3752, (2012).
Cobbs et al., "Expression of Nitric Oxide Synthase in Human Central Nervous System Tumors," Cancer Research, 55:727-730, (Feb. 1995).

(Continued)

*Primary Examiner* — Leigh C Maier
(74) *Attorney, Agent, or Firm* — Alston & Bird LLP

(57) ABSTRACT

Provided herein are compounds, compositions, and methods for modifying mucus, including modifying mucus using nitric oxide-releasing biopolymers (e.g., NO-releasing chitosan oligosaccharides). In some embodiments, a compound, composition, and/or method of the present invention modifies one or more properties of mucus to increase mucus clearance in a subject and/or prevents the growth or kills one or more pathogens present in mucus of a subject.

18 Claims, 12 Drawing Sheets

(56) References Cited

OTHER PUBLICATIONS

Dash et al., "Chitosan—A versatile semi-synthetic polymer in biomedical applications," Progress in Polymer Science, 36:981-1014, (2011).
Deppisch et al., "Gaseous nitric oxide to treat antibiotic resistant bacterial and fungal lung infections in patients with cystic fibrosis: a phase I clinical study," Infection, 44(4):513-520, (2016).
Dou et al., "Effects of chitosan oligosaccharides on neutrophils from glycogen-induced peritonitis mice model," Carbohydrate Polymers, 75:119-124, (2009) (epub Jul. 2008).
Duan, Jinyou and Dennis L. Kasper, "Oxidative depolymerization of polysaccharides by reactive oxygen/nitrogen species," Glycobiology, 21(4):401-409, (2011).
Duch et al., "Volatile anesthetics significantly suppress central and peripheral mammalian sodium channels," Toxicology Letters, 100-101:255-263, (1998).
Ehre et al., "Cystic Fibrosis: An Inherited Disease Affecting Mucin-Producing Organs," Int J Biochem Cell Biol., 52:136-145, (Jul. 2014).
Felley-Bosco, Emanuela, "Role of nitric oxide in genotoxicity: Implication for carcinogenesis," Cancer and Metastasis Reviews, 17:25-37, (1998).
Forier et al., "Transport of nanoparticles in cystic fibrosis sputum and bacterial biofilms by single-particle tracking microscopy," Nanomedicine, 8(6):935-949, (2013).
Freireich et al., "Quantitative Comparison of Toxicity of Anticancer Agents in Mouse, Rat, Hamster, Dog, Monkey, and Man," Cancer Chemotherapy Reports, 50(4):219-244, (May 1966).
Grenha et al., "The potential of chitosan for pulmonary drug delivery," J. Drug Del. Sci. Technol., 20(1):33-43, (2010).
Hassett et al., "Anaerobic metabolism and quorum sensing by Psuedomonas aeruginosa biofilms in chronically infected cystic fibrosis airways: rethinking antibiotic treatment strategies and drug targets," Advanced Drug Delivery Reviews, 54:1425-1443, (2002).
Henderson et al., "Cystic fibrosis airway secretions exhibit mucin hyperconcentration and increased osmotic pressure," Journal of Clinical Investigation, 124(7):3047-3060, (Jul. 2014).
Henke et al., "MUC5AC and MUC5B Mucins Increase in Cystic Fibrosis Airway Secretions during Pulmonary Exacerbation," American Journal of Respiratory and Critical Care Medicine, 175:816-821, (Jan. 2007).
Hetrick et al., "Bactericidal Efficacy of Nitric-Oxide Releasing Silica Nanoparticles," ACS Nano, 2(2):235-246, (2008).
Hill, David B. and Brian Button, "Establishment of respiratory air-liquid interface cultures and their use in studying mucin production, secretion, and function [Chapter 15]," Methods Mol. Biol., New York: Humana Press, pp. 245-258, (2012).
Høiby, Neils, "Recent advances in the treatment of Pseudomonas aeruginosa infections in cystic fibrosis," BMC Medicine, 9:32, 7 pages, (2011).
Hrabie, Joseph A. and Larry K. Keefer, "Chemistry of the Nitric Oxide-Releasing Dizeniumdiolate ("Nitrosohydroxylamine") Functional Group and Its Oxygen-Subsittuted Derivates," Chem. Rev., 102(4):1135-1154, (2002).
Ignarro et al., "Endothelium-derived relaxing factor produced and released from artery and vein is nitric oxide," Proc. Natl. Acad. Sci. USA, 84:9265-9269, (1987).
Ishii et al., "Facile enhancement of the deacetylation degree of chitosan by hydrothermal treatment in an imidazolium-based ionic liquid," Green Chem., 16:1764-1767, (2014).
Jain, Dharmendra and R. Banerjee, "Comparison of Ciprofloxacin Hydrochloride-Loaded Protein, Lipid, and Chitosan Nanoparticles for Drug Delivery," Journal of Biomedical Materials Research Part B: Applied Biomaterials, 86:105-112, (Dec. 2007).
Jenkins et al., "Roles of nitric oxide in tumor growth," Proc. Natl. Acad. Sci. USA, 92:4392-4396, (May 1995).
Jones et al., "Antimicrobial properties of nitric oxide and its application in antimicrobial formulations and medical devices," Appl. Microbiol. Biotechnol., 88(2):401-407, (2010).

Kean, T. and M. Thanou, "Biodegradation, biodistribution and toxicity of chitosan," Advanced Drug Delivery Reviews, 62:3-11, (2010).
Keefer, Larry K., "Nitric oxide-releasing compounds: From basic research to promising drugs," ChemTech, 28(8):30-35, (Aug. 1998).
Keefer, Larry K., "Progress Toward Clinical Application of the Nitric Oxide-Releasing Diazeniumdiolates," Annu. Rev. Pharmacol. Toxicol., 43:585-607, (2003).
Khutoryanskiy, Vitaliy V., "Advances in Mucoadhesion and Mucoadhesive Polymers," Macromolecular Bioscience, 11:748-764, (2011).
Klinger-Strobel et al., "A Novel Computerized Cell Count Algorithm for Biofilm Analysis," PLoS ONE, 11(5):30154937, 22 pages, (May 2016).
Lai et al., "Micro- and macrorheology of mucus," J. Adv. Drug Delivery Rev., 61 (2):86-100, (Feb. 2009).
Lu et al., "Nitric oxide-releasing amphiphilic poly(amidoamine) (PAMAM) dendrimers as antibacterial agents," Biomacromolecules, 14(10):3589-3598, (2013).
Lu et al., "Nitric oxide-releasing chitosan oligosaccharides as antibacterial agents," Biomaterials, 35(5): 1716-1724, (2014).
Lyczak et al., "Lung Infections Associated with Cystic Fibrosis," Clinical Microbiology Reviews, 15(2): 194-222, (Apr. 2002).
Maghami, Ghobad G. and George A. F. Roberts, "Evaluation of the viscometric constants for chitosan," Makromol. Chern., 189:195-200, (1988).
Manca et al., "PLGA, chitosan or chitosan-coated PLGA microparticles for alveolar delivery? A comparative study of particle stability during nebulization," Colloids and Surfaces B: Biointerfaces, 62:220-231, (2008).
Marietta et al., "Unraveling the biological signficance of nitric oxide," BioFactors, 2(4):219-225, (1990).
Matsui et al., "A physical linkage between cystic fibrosis airway surface dehydration and Pseudomonas aeruginosa biofilms," PNAS, 103(48):18131-18136, (Nov. 2006).
Menchicchi et al., "Structure of Chitosan Determines Its Interactions with Mucin," Biomacromolecules, 15:3550-3558, (2014).
Nablo et al., "Sol-Gel Derived Nitric-Oxide Releasing Materials that Reduce Bacterial Adhesion," J. Am. Chem. Soc., 123:9712-9713, (2001).
Napoli, Claudio and Louis J. Ignarro, "Nitric Oxide-Releasing Drugs," Annu. Rev. Pharmacol. Toxicol., 43:97-123, (2003).
Osman et al., "Spray dried inhalable ciprofloxacin powder with improved aerosolisation and antimicrobial activity," International Journal of Pharmaceutics, 449:44-58, (Apr. 2013).
Park et al., "Chitosan microspheres as an alvelolar macrophage delivery system of ofloxacin via pulmonary inhalation," International Journal of Pharmaceutics, 441:562-569, (2013) (epub. Nov. 2012).
Porporatto et al., "Chitosan induces different L-arginine metabolic pathways in resting and inflammatory macrophages," Biochemical and Biophysical Research Communications, 304:266-272, (2003).
Radomski et al., "The anti-aggregating properties of vascular endothelium: interactions between prostacyclin and nitric oxide," Br. J. Pharmac, 92:639-646, (1987).
Ramsey et al., "Mucin Agarose Gel Electrophoresis: Western Blotting for High-molecular-weight Glycoproteins," Journal of Visualized Experiments, 112:e54153, 6 pages, (2016).
Reighard, K. P. & Schoenfisch, M. H., "Antibacterial action of nitric oxide-releasing chitosan oligosaccharides against Pseudomonas aeruginosa under aerobic and anaerobic conditions," Antimicrob. Agents Chemother., 59:6506-6513, (2015).
Riccio and Schoenfisch, "Nitric oxide release: part I. Macromolecular scaffolds," Chem. Soc. Rev., 41(10):3731-3741, (2012).
Rossi et al., "Characterization of chitosan hydrochloride-mucin interaction by means of viscosimetric and turbidimetric measurements," European Journal of Pharmaceutical Sciences, 10:251-257, (2000).
Sashiwa et al., "Chemical modification of chitosan. Part 16: Synthesis of novel chitosan derivatives by substitution of hydrophilic amine using N-carboxyethylchitosan ethyl ester as an intermediate," Carbohydrate Research, 338(6):557-561, (2003).

(56) References Cited

OTHER PUBLICATIONS

Seabra et al., "State of the art, challenges and perspectives in the design of nitric oxidereleasing polymeric nanomaterials for biomedical applications," Biotechnology Advances, 33:1370-1379, (Jan. 2015).

Seagrave et al., "Effects of guaifenesin, N-acetylcysteine, and ambroxol on MUC5AC and mucociliary transport in primary differentiated human tracheal-bronchial cells," Respiratory Research, 13:98, 10 pages, (2012).

Shah et al., "In vivo effects of recombinant human Dnase I on sputum in patients with cystic fibrosis," Thorax, 51:119-125, (1996).

Slomberg, D.L et al., "Role of Size and Shape on Biofilm Eradication for Nitric Oxidereleasing Silica," ACS Appl. Mater. Interfaces, 5(19):9322-9329, (2013).

Sogias et al., "Why is Chitosan Mucoadhesive?", Biomacromolecules, 9(7):1837-1842, (2008).

Suk et al., "Rapid transport of muco-inert nanoparticles in cystic fibrosis sputum treated with N-acetyl cysteine," Nanomedicine (Lond)., 6(2):365-375, (Feb. 2011).

Suk et al., "The penetration of fresh undiluted sputum expectorated by cystic fibrosis patients by non-adhesive polymer nanoparticles," Biomaterials, 30(13):2591-2597, (May 2009).

Sun et al., "Nitric Oxide-Releasing Dendrimers as Antibacterial Agents," Biomacromolecules, 13(10):3343-3354, (2012).

Tamir et al., "DNA Damage by Nitric Oxide," Chemical Research in Toxicology, 9(5):821-827, (1996).

Tang et al., "Biodegradable polymer nanoparticles that rapidly penetrate the human mucus barrier," PNAS, 106(46):19268-19273, (Nov. 2009).

Thomsen et al., "Nitric oxide synthase activity in human breast cancer," British Journal of Cancer, 72:41-44, (1995).

Treggiari et al., "Approach to Eradication of Initial Pseudomonas aeruginosa Infection in Children With Cystic Fibrosis," Pediatric Pulmonology, 42:751-756, (2007).

Ungaro et al., "Dry powders based on PLGA nanoparticles for pulmonary delivery of antibiotics: Modulation of encapsulation efficiency, release rate and lung deposition pattern by hydrophilic polymers," Journal of Controlled Release, 157:149-159, (2012) (epub. 2011).

Valmikinathan et al., "Photocrosslinkable chitosan based hydrogels for neural tissue engineering," Soft Matter, 8(6):1964-1976, (Feb. 2012).

Wan, A., et al., "Effects of Molecular Weight and Degree of Acetylation on the Release of Nitric Oxide from Chitosan—Nitric Oxide Adducts," Journal of Applied Polymer Science, Wiley Periodicals, Inc., 117:2183-2188, (2010).

Wang et al., "Nitric oxide donors: chemical activities and biological applications," Chemical Reviews 102(4):1091-1134, (2002).

Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).

Zhang et al., "Chitosan Modification and Pharmaceutical/Biomedical Applications," Mar. Drugs, 8:1962-1987, (2010).

\* cited by examiner

COMPOUNDS, COMPOSITIONS AND METHODS FOR INHIBITING A PATHOGEN AND/OR MODIFYING MUCUS

RELATED APPLICATION INFORMATION

This application is a national stage application filed under 35 U.S.C. § 371 of International Application No. PCT/IB2018/052522, filed Apr. 10, 2018, which claims the benefit of and priority to U.S. Provisional Patent Application Ser. No. 62/483,655, filed Apr. 10, 2017, the disclosure of each of which is incorporated herein by reference in its entirety.

GOVERNMENT INTEREST

This invention was made with government support under AI 12029 and HL108808 awarded by The National Institutes of Health. The Government has certain rights in the invention.

FIELD OF THE INVENTION

The presently disclosed subject matter provides compounds, compositions, and methods for modifying mucus, including modifying mucus using nitric oxide-releasing biopolymers such as, for example, nitric oxide-releasing chitosan oligosaccharides.

BACKGROUND OF THE INVENTION

The discovery of the multifaceted role of nitric oxide (NO) in biology, physiology, and pathophysiology, see Marietta, M. A., et al., *BioFactors*, 2, 219-225 (1990), has led to the search for nitric oxide donors capable of controlled nitric oxide release. See, Keefer, L. K., *Chemtech*, 28, 30-35 (1998). To date, researchers have discovered that NO regulates a range of biological processes in the cardiovascular, gastrointestinal, genitourinary, respiratory, and central and peripheral nervous systems. See, Ignarro, L. J., *Nitric Oxide: Biology and Pathobiology*; Academic Press: San Diego, 2000; and Ignarro, L. J. et al., *Proc. Natl. Acad. Sci., USA.*, 84, 9265-9269 (1987). Furthermore, the discovery of NO as a vasodilator, and its identification as both an antibiotic and a tumoricidal factor, have made NO an attractive pharmaceutical candidate. See, for example, Radomski, M. W., et al., *Br. J. Pharmacol.*, 92, 639-646 (1987); Albina, J. E., and Reichner, J. S.; *Canc. Metas. Rev.*, 17, 19-53 (1998); Nablo, B. J., et al., *J. Am. Chem. Soc.*, 123, 9712-9713 (2001); Cobbs, C. S., et al., *Cancer Res.*, 55, 727-730 (1995); Jenkins, D. C., et al., *Proc. Natl. Acad. Sci., USA.*, 92, 4392-4396 (1995); and Thomsen, L. L., et al., *Br. J. Cancer.*, 72, 41-44 (1995).

Several nitric oxide donors have been reported, the most notable being N-diazeniumdiolates. Generally, N-diazeniumdiolate NO donors are small molecules synthesized by the reaction of amines with NO at elevated pressure and have been used, for example, to spontaneously generate NO in an aqueous solution. See, Hrabie, J. A. and Keefer, L. K., *Chem. Rev.*, 102, 1135-1154 (2002).

Cystic fibrosis (CF) is a life-limiting, genetically inherited disorder affecting roughly 30,000 people in the United States of America (US) and 70,000 people worldwide (Heiby, N. *BMC Med.*, 9, 32-39 (2011); Treggiari, M. M., et al., *Pediatric Pulmonology*, 42, 751-756 (2007)). A defect in the CF transmembrane conductance regulator protein results in the accumulation of mucus in and obstructs normal function of the lungs, liver, pancreas, gastrointestinal tract, and reproductive system (Ehre, C., et al., *The International Journal of Biochemistry & Cell Biology*, 52, 136-145 (2014)). As mucus accumulates and thickens in the CF lungs, airway clearance is impaired, fostering bacteria colonization (Matsui, H., et al., *P.N.A.S.*, 103, 18131-18136 (2006)). This thickened mucus layer generates an environment that protects bacteria from immune cells and promotes biofilm formation (Hassett, D. J., et al., *Adv. Drug Delivery Rev.*, 54, 1425-1443 (2002)). Chronic infections are accompanied by persistent inflammation and an ultimate decline in lung function (Hassett, D. J., et al., *Adv. Drug Delivery Rev.*, 54, 1425-1443 (2002)). As a result, respiratory complications related to chronic bacterial infections are the leading cause of death for CF patients (Lyczak, J. B., et al., *Clinical Microbiology Reviews*, 15, 194-222 (2002)).

Therapeutic strategies to explore the activities of nitric oxide donors are problematic in part because the nitric oxide delivery systems known in the art release or donate nitric oxide indiscriminately.

SUMMARY OF THE INVENTION

Aspects of the present invention include methods of modifying one or more properties of mucus using a nitric oxide (NO)-releasing biopolymer such as, for example, a NO-releasing polyglucosamine, as described herein.

One aspect of the present invention is directed to a method of modifying mucus in a subject in need thereof, the method comprising: administering a NO-releasing biopolymer as described herein to the subject, wherein the NO-releasing biopolymer is mucoadhesive and is administered to the subject in an amount that is mucolytic and antimicrobial, thereby modifying mucus in the subject.

Another aspect of the present invention is directed to a method of modifying mucus, the method comprising: contacting a NO-releasing biopolymer as described herein to mucus, wherein the NO-releasing biopolymer is mucoadhesive and in an amount that is mucolytic and antimicrobial, thereby modifying the mucus.

An additional aspect of the present invention is directed to a method of increasing mucus clearance in a subject, the method comprising administering to the subject a NO-releasing biopolymer as described herein.

Another aspect of the present invention is directed to a method of decreasing mucus viscosity and/or elasticity in a subject, the method comprising administering to the subject a NO-releasing biopolymer as described herein.

A further aspect of the present invention is directed to a method of decreasing mucus viscosity and/or elasticity, the method comprising contacting mucus with a NO-releasing biopolymer as described herein.

Another aspect of the present invention is directed to a method of inhibiting or killing a pathogen in mucus, the method comprising contacting mucus with a NO-releasing biopolymer as described herein. Some embodiments include administering to a subject a NO-releasing biopolymer as described herein to inhibit or kill a pathogen in mucus of the subject.

A further aspect of the present invention is directed to a method of inhibiting or killing a pathogen in mucus, the method comprising administering to a subject a NO-releasing biopolymer as described herein.

In some embodiments, the subject matter disclosed herein is directed to a NO-releasing biopolymer (e.g., a polyglucosamine) that contains a covalently bound nitric oxide releasing moiety, i.e. a NO donor. In some embodiments, the NO-releasing biopolymer comprises a polyglucosamine, optionally that comprises at least one structural unit in the polyglucosamine backbone having the structure of formula I. Optionally, at least one structural unit of the polyglucosamine further comprises the structure of formula II. In some embodiments, a NO-releasing biopolymer as described herein functions as an antimicrobial agent and/or degrades mucin, such as, e.g., mucin from human bronchial epithelial cell cultures and/or clinical sputum samples collected from patients with cystic fibrosis.

In some embodiments, the subject matter disclosed herein is directed to methods of treating a disease state in a subject comprising administering a NO-releasing biopolymer as described herein. In some embodiments, a NO-releasing polyglucosamine comprising at least one structural unit of formula I and optionally, further comprising at least one structural unit of formula II is administered to the subject. In further embodiments, the NO-releasing biopolymer functions as a broad spectrum antibiotic and/or decreases the viscoelasticity of mucus and/or CF sputum.

In some embodiments, the subject matter disclosed herein is directed to a pharmaceutical composition comprising a NO-releasing biopolymer as described herein and a pharmaceutically acceptable carrier, excipient or diluent. In some embodiments, a pharmaceutical composition of the present invention comprises a NO-releasing polyglucosamine as described herein and a pharmaceutically acceptable carrier, excipient or diluent. The NO-releasing polyglucosamine may comprise at least one structural unit of formula I and optionally at least one structural unit of formula II.

In some embodiments, the subject matter disclosed herein is directed to methods of preparing a NO-releasing biopolymer as described herein, such as, for example, a NO-releasing polyglucosamine comprising at least one structural unit of formula I and optionally at least one structural unit of formula II.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the embodiments that follow, such description being merely illustrative of the present invention.

DETAILED DESCRIPTION

Figure 1:
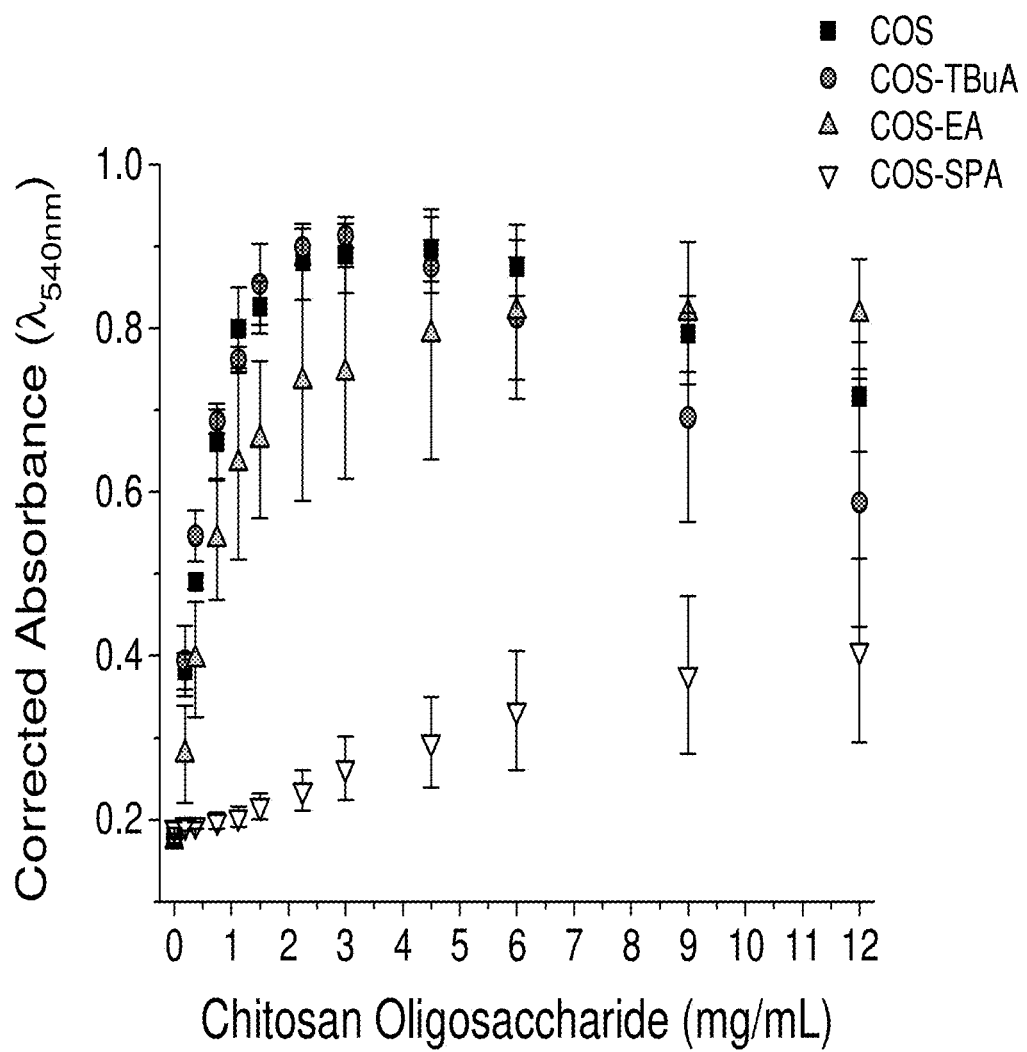
FIG. 1 shows the turbidimetric titration of gastric pig mucin (GPM) with modified chitosan oligosaccharides.

The present invention is now described more fully hereinafter with reference to the accompanying drawings, in which embodiments of the invention are shown. The present invention may, however, be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all terms (including technical and scientific terms) used herein will have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" NO releasing moiety can mean a single or a multiplicity.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value, such as an amount of a compound or agent of this invention, dose, time, temperature, and the like, is meant to encompass variations of ±20%, ±10%, ±5%, ±1%, ±0.5%, or even ±0.1% of the specified amount. A range provided herein for a measurable value may include any other range and/or individual value therein.

The term "consists essentially of" (and grammatical variants), as applied to the compositions of this invention means the composition can contain additional components, as long as the additional components do not materially alter the composition.

As used herein, the terms "increase," "increases," "increased," "increasing", "improve", "enhance", and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction", "inhibit", and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "-," it will be understood that the attachment is read from left to right.

Unless otherwise stated, structures depicted herein are meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

"Mucoadhesion" as used herein refers to adherence of a compound to mucin, mucus, and/or a mucosal surface in a subject. "Mucoadhesive" as used herein in reference to a compound means that the compound that can adhere to mucin, mucus, and/or a mucosal surface in a subject. A compound may adhere to mucin, mucus, and/or a mucosal surface using any type of bond, such as, e.g., covalent, ionic, and/or hydrogen bond(s). In some embodiments, a compound of the present invention (i.e., a NO-releasing biopolymer) is mucoadhesive.

In some embodiments, a compound of the present invention has improved mucoadhesion compared to a control (e.g., an unmodified biopolymer and/or non-NO-releasing biopolymer such as, e.g., chitosan that does not comprise a NO donor). In some embodiments, the control may be chitosan (e.g., a medium molecular weight chitosan having a viscosity of about 200-800 centipoise when present in a 1% acetic acid solution in an amount of 1% by weight and measured at 25° C.) and/or a modified chitosan without a NO donor (e.g., 2-methylaziridine-modified chitosan that does not contain a NO donor). The amount or degree of mucoadhesion for a compound may be measured by methods known to those of skill in the art such as, e.g., by measuring the turbidity of mucin solutions comprising the compound, optionally by measuring the corrected absorbance, and/or by measuring the turbidity of mucin solutions. For example, the amount or degree of mucoadhesion for a compound may be measured with a mucin solution containing a compound of the present invention. The mucin solution may be prepared by combining 960 mg of gastric pig mucin in 250 mL of sterile phosphate buffer (PB) at 4° C. for 18 h with insoluble components removed (e.g., by centrifugation at 1,500×g, 4° C., 0.5 h), optionally at pH 6.5. The mucin solution may be combined with a solution containing a compound of the present invention to form a combined solution. The solution containing a compound of the present invention may be a sterile PB that includes the compound at a concentration of about 0.1 mg/mL to about 60 mg/mL. The combined solution may be prepared by combining 236 μL of the mucin solution with 34 μL of the solution containing a compound of the present invention. Absorbance of the combined solution can be read at 540 nm. In some embodiments, the combined solution may be incubated for 1 h at 37° C., optionally with gentle shaking (e.g., 100 rpm), and then absorbance can be read at 540 nm. A corrected absorbance can be obtained by subtracting the absorbance of the solution containing the compound (i.e., without mucin) from the combined solution absorbance. In some embodiments, increased turbidity of a solution containing a compound of the present invention and mucin compared to a control solution indicates improved mucoadhesion. The control solution may be a solution containing mucin and a lower concentration of the compound or may be a solution comprising an unmodified and/or non-NO-releasing biopolymer (e.g., a non-NO-releasing chitosan).

In some embodiments, the amount or degree of mucoadhesion for a compound of the present invention may be measured by a decrease in turbidity of a mucin solution comprising the compound upon addition of sodium chloride to the mucin solution. Sodium chloride may be added to the mucin solution containing the compound in an amount to achieve about 140 mM NaCl, optionally at pH 6.5. A greater decrease in turbidity upon addition of sodium chloride to a mucin solution comprising a first compound can indicate that the first compound has a lower degree of mucoadhesion to mucin relative to a second compound that had less of a decrease in turbidity upon addition of sodium chloride to a mucin solution comprising the second compound.

In some embodiments, the amount or degree of mucoadhesion for a compound may be measured and/or quantified by zeta potential of a mucin solution containing the compound, optionally a mucin solution at pH 6.5. For example, a mucin solution for measuring zeta potential may be as described above, or may be prepared by combining 10 mg of gastric pig mucin in 10 mL of sterile PB at 4° C. for 18 h with insoluble components removed (e.g., by centrifugation at 1,500×g, 4° C., 0.5 h). A compound of the present invention may be added to the mucin solution, optionally with stirring, and the zeta potential may be measured, optionally after being incubated for 1 h at 37° C. A mucin solution comprising a compound of the present invention and having an increased zeta potential compared to the zeta potential for a control mucin solution (e.g., a mucin solution without the compound) can indicate the amount or degree of mucoadhesion for the compound. In some embodiments, a mucin solution comprising a compound of the present invention has a zeta potential that is increased by at least 1, 2, or 3 mV compared to the zeta potential of a control mucin solution (e.g. a mucin solution without the compound).

Provided according to embodiments of the present invention are compounds, compositions, and/or methods of modifying mucus. In some embodiments, a compound, composition, and/or method of the present invention may modify one or more physical and/or biophysical properties of mucus and/or may increase (e.g., by about 10% or more) mucociliary clearance of mucus and/or pulmonary function in a subject. In some embodiments, a compound, composition, and/or method of the present invention may decrease (e.g., by about 10% or more) or eliminate a pathogen in mucus and/or a subject. Thus, according to some embodiments, a compound, composition, and/or method of the present invention may modify one or more physical and/or biophysical properties of mucus and may decrease or kill one or more pathogens in mucus and/or a subject. A modification to mucus and/or the amount of a pathogen in mucus and/or a subject may be determined within about 24 hours (e.g., within about 20, 18, 12, 10, 8, 6, 4, or 2 hours) of administering a NO-releasing biopolymer of present invention to the subject and/or contacting a NO-releasing biopolymer of present invention to the mucus.

In some embodiments of the present invention provided is a monotherapy for increasing mucus clearance and/or degradation in a subject and decreasing one or more pathogens in a subject, such as, e.g., one or more pathogens in the mucus of the subject. As used herein, the term "monotherapy" refers to a single agent that is used to treat two or more conditions, such as, e.g., a bacterial infection and cystic fibrosis. The monotherapy may be administered to a subject one or more times (e.g., 1, 2, 3, 4, 5, 6 or more times) in a treatment period. In some embodiments, a method of the present invention comprises administering a NO-releasing biopolymer as a monotherapy and, responsive to the monotherapy, mucus clearance is increased in the subject, at least one pathogen present in mucus of the subject is inhibited or killed, mucus degradation is increased in the subject, and/or mucus viscosity and/or elasticity in the subject is decreased.

A method of the present invention may comprise administering to a subject and/or contacting to mucus a NO-releasing biopolymer of the present invention such as, e.g., a NO-releasing polyglucosamine of the present invention. A "biopolymer" as used herein refers to a polymer that can be produced by a living organism or a derivative thereof. Exemplary biopolymers include, but are not limited to, proteins, peptides, oligonucleotides, oligosaccharides, and/or polysaccharides. As one of ordinary skill in the art will understand, a biopolymer may be synthetically obtained (e.g., through laboratory synthesis) and/or obtained and/or derived from nature (e.g., from a living or previously living organism). Therefore, the biopolymer may be the same as a polymer found in nature (i.e., a native biopolymer) or may be a derivative thereof. For example, a biopolymer of the present invention may be a derivative of a polymer produced by a living organism, the derivative caused by the synthetic method used to obtain or isolate the biopolymer from nature. In some embodiments, the biopolymer has an available nitrogen (e.g., an available nitrogen in its backbone and/or pendant therefrom) that can be derivatized with a NO donor such as, e.g., according to the methods described herein to form a NO-releasing polyglucosamine. In some embodiments, the biopolymer comprises one or more secondary amine(s), one or more of which may be derivatized and/or converted to a NO donor, such as, for example, by converting the secondary amine to a NO donor in the presence of a strong base and gaseous nitric oxide.

Further exemplary biopolymers include, but are not limited to, chitosans, starches (including amylose and/or amylopectin), hemicelluloses, lignins, celluloses, chitins, alginates, dextrans, pullanes, polyhydroxyalkanoates, fibrins, cyclodextrins, proteins (e.g., soy protein), other polysaccharides (e.g., pectin), and/or polylactic acids.

A biopolymer used in a method of the present invention may have a molecular weight of about 20,000 Daltons or less such as, e.g., about 10,000 Daltons or less. In some embodiments, the biopolymer may have a molecular weight of about 20,000, 19,000, 18,000, 17,000, 16,000, 15,000, 14,000, 13,000, 12,000, 11,000, 10,000, 9,000, 8,000, 7,000, 6,000, 5,000, 4,000, 3,000, 2,000, or 1,000 Daltons. In some embodiments, the biopolymer may have a molecular weight of about 1,000 Daltons to about 20,000 Daltons, about 1,000 Daltons to about 10,000 Daltons, or about 1,000 Daltons to about 10,000 Daltons. In some embodiments, the biopolymer may be polydisperse. In some embodiments, the biopolymer may be water soluble or may be functionalized to be water soluble.

An NO-releasing biopolymer of the present invention is a biopolymer that comprises one or more NO donors (e.g., 1, 2, 5, 10, 50, 100, 200, or more). In some embodiments, a NO-releasing biopolymer of the present invention has at least about 1%, 5%, 10%, 15%, 20%, 25%, 30%, 35%, 40%, 45%, 50%, 55%, 60%, 65%, 70%, 75%, 80%, 85%, 90%, 95%, 98%, or 100% of the monomeric units of the polymer backbone functionalized with a NO donor. In some embodiments, a NO-releasing biopolymer of the present invention has at least about 1% to about 20% of the monomeric units of the polymer backbone functionalized with a NO donor. In some embodiments, a NO-releasing biopolymer of the present invention has at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% NO by weight of the biopolymer.

In some embodiments, the NO-releasing biopolymer of the present invention is a NO-releasing polyglucosamine of the present invention. A NO-releasing polyglucosamine of the present invention is interchangeably referred to herein as a NO-releasing chitosan oligosaccharide. In some embodiments, a NO-releasing polyglucosamine of the present invention is prepared from and/or comprises a medium molecular weight chitosan. In some embodiments, a NO-releasing polyglucosamine of the present invention is prepared from and/or comprises a medium molecular weight chitosan having a viscosity of about 200 to about 800 centipoise when present in a 1% acetic acid solution in an amount of 1% by weight and measured at 25° C. In some embodiments, a NO-releasing polyglucosamine of the present invention is prepared from and/or comprises deacetylated chitosan such as, for example, chitosan that is about 5% to about 100%, about 10% to about 50%, about 75% to about 85%, about 70% to about 95%, about 95% to about 98%, about 50% to about 80%, about 90% to about 98%, or about 80% to about 90% deacetylated. In some embodiments, a NO-releasing polyglucosamine of the present invention is prepared from and/or comprises a chitosan (e.g., a medium molecular weight chitosan optionally having a viscosity of about 200 to about 800 centipoise when present in a 1% acetic acid solution in an amount of 1% by weight and measured at 25° C.) that is about 50%, 55%, 60%, 65%, 70%, 80%, 85%, 90%, 95%, 98%, or 100% deacetylated.

In some embodiments, a polyglucosamine of the present invention comprises at least one structural unit of Formula I:

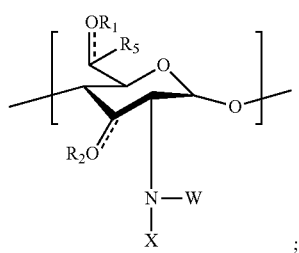

and optionally at least one structural unit of Formula II:

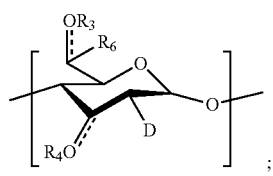

wherein,
$R_1$, $R_2$, $R_3$ and $R_4$, if present, are each independently selected from the group consisting of hydrogen, —(C=O)$C_{1-5}$ alkyl, and $C_{1-5}$ alkyl;
----, in each instance, is a single or double bond, wherein in each instance where it is a double bond, $R_1$, $R_2$, $R_3$ or $R_4$ attached to the double bond-O is absent; when $R_1$ is absent, $R_5$ is hydrogen, hydroxyl, $C_{1-5}$ alkyl or $C_{1-5}$ alkoxy; when $R_3$ is absent, $R_6$ is hydrogen, hydroxyl, $C_{1-5}$ alkyl or $C_{1-5}$ alkoxy;

wherein in each instance where it is a single bond, $R_1$, $R_2$, $R_3$ or $R_4$ attached to the double bond-O is present; when $R_1$ is present, $R_5$ is hydrogen; when $R_3$ is present, $R_6$ is hydrogen;

W is -(Q-A)$_p$-B, -Q-A-B, or —$C_{1-20}$ alkyl-A-B;
Q is —(CR$_c$R$_d$)$_v$—;
  wherein R$_c$ and R$_d$ are, in each instance, independently hydrogen or $C_{1-5}$ alkyl; and v is an integer from 2 to 6;
p is an integer from 1 to 100;
A is

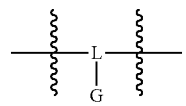

wherein, L is S, O or N; and
  G, in each instance, is independently, hydrogen, or is taken together with L to form a nitric oxide donor or is absent;
X is hydrogen, $C_{1-5}$ alkyl or is taken together with N to form a nitric oxide donor;
B is absent or is selected from the group consisting of hydrogen, hydroxyl, $C_{1-5}$ alkyl, or —Y—Z, wherein Y is a spacer and Z is a polymer, terminus, or $C_{1-20}$ alkyl;
D is —NR$_a$R$_b$, wherein R$_a$ and R$_b$ are independently selected from the group consisting of hydrogen, formyl, —(C=O)$C_{1-5}$ alkyl, $C_{1-5}$ alkyl and $C_{1-5}$ alkyl ester;
or D is

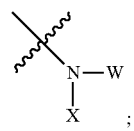

wherein the polyglucosamine comprises at least one nitric oxide donor; and
wherein G is taken together with L to form the at least one nitric oxide donor or X is taken together with N to form the at least one nitric oxide donor.

In some embodiments, a NO-releasing biopolymer (e.g., NO-releasing polyglucosamine) of the present invention is mucoadhesive. In some embodiments, a NO-releasing biopolymer of the present invention is mucoadhesive and is more mucoadhesive than chitosan (e.g., a medium molecular weight chitosan having a viscosity of about 200-800 centipoise when present in a 1% acetic acid solution in an amount of 1% by weight and measured at 25° C.) and/or a modified chitosan without a NO donor (e.g., 2-methylaziridine-modified chitosan that does not contain a NO donor). In some embodiments, a NO-releasing biopolymer of the present invention is mucoadhesive and is more mucoadhesive than a non-NO-releasing biopolymer (e.g., chitosan (e.g., a medium molecular weight chitosan having a viscosity of about 200-800 centipoise when present in a 1% acetic acid solution in an amount of 1% by weight and measured at 25° C.)) by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, or more.

A NO-releasing biopolymer of the present invention may be positively charged and/or have an overall positive charge. Electrostatic interactions between a NO-releasing biopolymer of the present invention and mucin may facilitate and/or aid in mucoadhesion of the NO-releasing biopolymer to mucin, mucus, and/or a mucosal surface in a subject.

In some embodiments, a NO-releasing biopolymer of the present invention may be administered to a subject at a lower dose compared to a control compound. The control compound can be a non-mucoadhesive biopolymer such as, e.g., a NO-releasing biopolymer that is not mucoadhesive and which optionally may deliver the same amount and/or rate of NO as a mucoadhesive NO-releasing biopolymer of the present invention. In some embodiments, the control compound can be a NO-releasing small molecule (e.g., an organic and/or inorganic compound having a molecular weight of less than 500 Daltons and comprising at least one NO donor). The dose of the NO-releasing biopolymer of the present invention may be lower than the dose of the control compound, optionally to achieve the same or similar result, by at least about 5%, 10%, 15%, 20%, 25%, 30%, 35%, 40%, 45%, 50%, 55%, 60%, 65%, 70%, 75%, 80%, 85%, 90%, 95% or more. For example, in some embodiments, a NO-releasing biopolymer of the present invention is mucoadhesive and may be administered to a subject at a lower dose compared to a NO-releasing biopolymer that is not mucoadhesive, which optionally may deliver the same amount and/or rate of NO as a mucoadhesive NO-releasing biopolymer of the present invention, and/or compared to a NO-releasing small molecule. In some embodiments, a mucoadhesive NO-releasing biopolymer (e.g. NO-releasing polyglucosamine) of the present invention may be administered in an amount that modifies one or more properties of mucus and this amount is less than an amount of a NO-releasing biopolymer that is not mucoadhesive to achieve the same or similar modification to mucus, optionally wherein the non-mucoadhesive biopolymer delivers the same amount and/or rate of NO as the mucoadhesive NO-releasing biopolymer, and/or less than an amount of a NO-releasing small molecule.

In some embodiments, a mucoadhesive NO-releasing biopolymer of the present invention may be administered to a subject in a therapeutically effective amount and/or treatment effective amount and this amount is less than the amount of a control compound such as, e.g., a non-mucoadhesive biopolymer, which optionally delivers the same amount and/or rate of NO as the mucoadhesive NO-releasing biopolymer, and/or a NO-releasing small molecule, to achieve the same or similar therapeutic result. The therapeutically effective amount and/or treatment effective amount of the NO-releasing biopolymer of the present invention may be lower than the amount of the control compound by at least about 5%, 10%, 15%, 20%, 25%, 30%, 35%, 40%, 45%, 50%, 55%, 60%, 65%, 70%, 75%, 80%, 85%, 90%, 95% or more. In some embodiments, administration of a NO-releasing biopolymer of the present invention does not produce systemic effects from the administration of nitric oxide, such as, for example, in a treatment effective amount.

In some embodiments, a NO-releasing biopolymer is administered at a dose that is mucolytic. "Mucolytic" as used herein in reference to a compound (e.g., a NO-releasing biopolymer of the present invention) means that the compound is administered at a dose that can break down mucus and/or decrease mucus viscosity and/or elasticity.

In some embodiments, a NO-releasing biopolymer and/or method of the present invention may decrease mucus viscosity and/or elasticity. Mucus viscosity and/or elasticity may be decreased by at least about 10% compared to the mucus viscosity and/or elasticity in the absence of a NO-releasing biopolymer and/or method of the present invention and/or prior to a method of the present invention. In some embodiments, mucus viscosity and/or elasticity is reduced by about 10%, 15%, 20%, 25%, 50%, 55%, 60%, 65%, 70%, 75%, 80%, 85%, 90%, 95%, 97%, or 100%, or any range comprising any two individual values therein, compared to the mucus viscosity and/or elasticity in the absence of a NO-releasing biopolymer and/or method of the present invention and/or prior to a method of the present invention. For example, in some embodiments, the mucus viscosity and/or elasticity may be decreased by an amount in a range of about 65% to about 95%, about 75% to about 95%, or about 65% to about 90%. In some embodiments, viscosity and/or elasticity may be reduced by an amount that is statistically greater than an appropriate control (e.g., a control compound as described herein). Mucus viscosity and/or elasticity may be determined in vitro.

In some embodiments, a NO-releasing biopolymer and/or method of the present invention may decrease mucus viscosity and/or elasticity in an amount greater (e.g., at least 5%, 10%, 15%, or 20% greater) than a conventional mucolytic therapy such as, e.g., administration of N-acetylcysteine or dornase alfa. In some embodiments, a NO-releasing biopolymer and/or method of the present invention may decrease mucus viscosity and/or elasticity in less time after administration of the NO-releasing biopolymer than the amount of time to achieve the same decrease in mucus viscosity and/or elasticity upon administration of a conventional mucolytic therapy such as, e.g., administration of N-acetylcysteine or dornase alfa.

"Elasticity" as used herein in reference to mucus refers to the ability of mucus to return to an original shape after experiencing a deformation in shape due to an external force (e.g., solid behavior). "Viscosity" as used herein in reference to mucus refers to a measure of the resistance of mucus to deformation (e.g., liquid behavior) upon application of a force (e.g., shear stress or tensile stress). A higher mucus viscosity means that the mucus is less deformable. "Viscoelasticity" as used herein in reference to mucus refers to a characteristic of mucus which exhibits both viscous and elastic characteristics when undergoing deformation.

A NO-releasing biopolymer (e.g., NO-releasing polyglucosamine) and/or method of the present invention may reduce mucus viscosity and/or elasticity by at least about 10% at about 15, 30, 45, 60, or 90 minutes, or about 2, 3, 4, 5, 6, 7, 8, 9, 10, 11, 12, 13, 14, 15, 16, 17, 18, 19, 20, 21, 22, 23, 24 hours or more after contact and/or administration of the NO-releasing biopolymer to mucus and/or a subject. In some embodiments, a NO-releasing biopolymer and/or method of the present invention may decrease mucus viscosity and/or elasticity by at least about 50%, 75%, 80%, or 90% at about 1, 6, 12, or 24 hour(s) after contact and/or administration of the NO-releasing biopolymer to mucus and/or a subject.

In some embodiments, a NO-releasing biopolymer (e.g., NO-releasing polyglucosamine) and/or method of the present invention may decrease mucus accumulation in a subject, such as, for example, mucus accumulation in an airway, lung, bronchi, and/or trachea in the subject. The NO-releasing biopolymer and/or method may decrease mucus accumulation in the subject by about 10%, 15%, 20%, 25%, 50%, 55%, 60%, 65%, 70%, 75%, 80%, 85%, 90%, 95%, 97%, or 100% compared to mucus accumulation in the absence of a NO-releasing biopolymer and/or method of the present invention and/or prior to a method of the present invention. In some embodiments, mucus accumulation may be reduced by an amount that is statistically greater than an appropriate control (e.g., a control compound as described herein). Mucus accumulation may be determined in vitro.

A NO-releasing biopolymer (e.g., NO-releasing polyglucosamine) and/or method of the present invention may reduce (e.g., by about 10% or more) the size of mucin and/or mucin multimers, optionally determined in vitro such as, e.g., using methods known to those of skill in the art such as, e.g., by measuring mucin migration distance optionally using gel electrophoresis. In some embodiments, a NO-releasing biopolymer and/or method of the present invention may modify the charge on mucin and/or mucin multimers, optionally determined in vitro such as, e.g., using methods known to those of skill in the art such as, e.g., by measuring zeta potential of mucin solutions and/or mucin migration distance optionally using gel electrophoresis. In some embodiments, a NO-releasing biopolymer and/or method of the present invention may modify and/or disrupt the three-dimensional network of mucin, optionally determined in vitro such as, e.g., using methods known to those of skill in the art such as, e.g., immunohistochemical detection and/or measuring mucin migration distance optionally using gel electrophoresis. In some embodiments, a NO-releasing biopolymer and/or method of the present invention may reduce (e.g., by about 10% or more) the number and/or length of filaments of mucin in mucus, optionally determined in vitro such as, e.g., using methods known to those of skill in the art such as, e.g., immunohistochemical detection and/or measuring mucin migration distance optionally using gel electrophoresis. In some embodiments, a NO-releasing biopolymer and/or method of the present invention may alter DNA present in the mucus, optionally determined in vitro such as, e.g., using methods known to those of skill in the art such as, e.g., immunohistochemical detection and/or measuring mucin migration distance optionally using gel electrophoresis. For example, the NO-releasing biopolymer and/or method may cleave DNA present in the mucus, such as, e.g., by NO-mediated DNA cleavage. In some embodiments, a NO-releasing biopolymer and/or method of the present invention may reduce (e.g., by about 10% or more) the concentration of one or more mucins (e.g., MUC5AC and/or MUC5B) present in the mucus, optionally determined in vitro such as, e.g., using methods known to those of skill in the art such as, e.g., immunohistochemical detection and/or gel electrophoresis.

In some embodiments, a NO-releasing biopolymer (e.g., NO-releasing polyglucosamine) and/or method of the present invention may increase mucus clearance in a subject. Mucus clearance may be increased by at least about 10% compared to mucus clearance in the absence of a NO-releasing biopolymer and/or method of the present invention and/or prior to a method of the present invention. In some embodiments, mucus clearance is increased by about 10%, 15%, 20%, 25%, 50%, 55%, 60%, 65%, 70%, 75%, 80%, 85%, 90%, 95%, 100%, 150%, 200%, 300%, 400%, or more compared to mucus clearance in the absence of a NO-releasing biopolymer and/or method of the present invention and/or prior to a method of the present invention.

In some embodiments, a NO-releasing biopolymer and/or method of the present invention may increase mucus clearance in a subject in an amount greater (e.g., at least 5%, 10%, 15%, or 20% greater) than a conventional mucolytic therapy such as, e.g., administration of N-acetylcysteine or dornase alfa. In some embodiments, a NO-releasing biopolymer and/or method of the present invention may increase mucus clearance in a subject in less time after administration of the NO-releasing biopolymer than the amount of time to achieve the same increase in mucus clearance in a subject upon administration of a conventional mucolytic therapy such as, e.g., administration of N-acetylcysteine or dornase alfa.

According to some embodiments, a NO-releasing biopolymer (e.g., NO-releasing polyglucosamine) of the present invention is antimicrobial and/or a method of the present invention may administer a NO-releasing biopolymer of the present invention at a dose that is antimicrobial. In some embodiments, a NO-releasing biopolymer is administered to a subject and/or contacted to mucus at a dose effective to inhibit growth of a pathogen (e.g., bacteria) and/or kill a pathogen. In some embodiments, a NO-releasing biopolymer and/or method of the present invention provides and/or delivers nitric oxide to the subject and/or mucus in an amount that is effective to inhibit growth of a pathogen and/or kill a pathogen. In some embodiments, a NO-releasing biopolymer and/or method of the present invention provides and/or delivers nitric oxide to the subject and/or mucus in an amount that is equal to or less than (e.g., at least 5%, 10%, 15%, or 20% less) the concentration effective to inhibit growth of a pathogen and/or kill a pathogen for nitric oxide alone (e.g., gaseous NO).

A NO-releasing biopolymer (e.g., NO-releasing polyglucosamine) and/or a method of the present invention may inhibit growth and/or kill one or more (e.g., 1, 2, 3, 4, 5, 6, 7, 8, 9, 10, 11, or more) pathogen(s). In some embodiments, a NO-releasing biopolymer may be a broad spectrum antimicrobial. A NO-releasing biopolymer and/or a method of the present invention may inhibit growth and/or kill one or more aerobic and/or anaerobic pathogen(s) and/or may inhibit growth and/or kill one or more pathogen(s) under aerobic and/or anaerobic conditions. In some embodiments, a NO-releasing biopolymer and/or a method of the present invention may inhibit growth and/or kill one or more gram-negative bacteria and/or gram-positive bacteria. In some embodiments, a NO-releasing biopolymer and/or a method of the present invention may inhibit growth and/or kill gram-negative bacteria and gram-positive bacteria under aerobic and anaerobic conditions.

In some embodiments, a method of the present invention comprises administering and/or contacting a NO-releasing biopolymer of the present invention to a subject and/or mucus in an amount that is equal to or greater than the amount effective to prevent the visible growth of the pathogen. In some embodiments, a method of the present invention comprises administering and/or contacting a NO-releasing biopolymer of the present invention to a subject and/or mucus in an amount that is equal to or greater than the amount effective to kill the pathogen. As used herein, the terms "contact", "contacting", and the like, refer to two or more substances in close proximity so that an effect may occur. For example, in embodiments, the mucus of a subject may be in contact with a NO-releasing biopolymer such that a modification of mucus can occur, e.g. an increase in the mucus clearance in the subject.

Example pathogens include, but are not limited to, *Staphylococcus aureus* including methicillin-resistant *S. aureus* (MRSA) and methicillin-sensitive *S. aureus* (MSSA), *Pseudomonas aeruginosa* (e.g., mucoid and non-mucoid *Pseudomonas aeruginosa*), *Burkholderia cepacia*, *Achromobacter Xylosoxidans*, *Stenotrophomonas maltophillia*, *Klebsiella pneumoniae*, *Achromobacter xylosidans*,

*Scedosporium apiospermum*, and *mycobacterium* including *Mycobacterium avium, Mycobacterium abscessus*, and *Mycobacterium intracelullare*. As used herein, the term "*mycobacterium*" refers to a family of bacteria with over 150 recognized species and which is a genus of *Actinobacteria*. *Mycobacterium* include, but are not limited to, pathogens known to cause diseases such as tuberculosis and leprosy. Further non-limiting examples of *mycobacterium* are *Mycobacterium tuberculosis, Mycobacterium gordonae, Mycobacterium kansasii*, and *Mycobacterium nonchromogenicum*, and *Mycobacterium ulcerans*. In some embodiments, the pathogen is a mycobacteria. In some embodiments, the pathogen is a nontuberculosis mycobacteria, such as, but not limited to, nontuberculosis *Mycobacteria abscessus* and nontuberculosis *Mycobacteria avium*. In some embodiments, the pathogen is an antibiotic resistant pathogen and/or a super bug. As used herein, the term "super bug" refers to a pathogen (e.g., a bacteria) that is multidrug resistant and that cannot be killed using two or more antimicrobials (e.g., antibiotics).

In some embodiments, a NO-releasing biopolymer (e.g., NO-releasing polyglucosamine) and/or a method of the present invention may inhibit growth and/or kill one or more pathogens that is resistant to one or more antibiotics, such as, but not limited to, a pathogen that is resistant to conventional CF antibiotics. In some embodiments, a NO-releasing biopolymer and/or a method of the present invention may inhibit growth and/or kill mucoid and/or non-mucoid *Pseudomonas aeruginosa*. In some embodiments, a NO-releasing biopolymer and/or a method of the present invention may inhibit growth and/or kill a pathogen resistant to conventional CF antibiotics, mucoid and/or non-mucoid *Pseudomonas aeruginosa, Burkholderia cepacia* complex species, methicillin resistant *Staphylococcus aureus*, nontuberculosis *Mycobacteria abscessus*, nontuberculosis *Mycobacteria avium, Achromobacter xylosidans*, and/or *Scedosporium apiospermum*.

In some embodiments, a method of the present invention comprises contacting and/or administering a NO-releasing biopolymer of the present invention to mucus and/or a subject in an amount that is antimicrobial and that decreases the viscosity and/or elasticity of mucus. The amount of the NO-releasing biopolymer may deliver and/or administer nitric oxide in an amount that is less than the amount of nitric oxide alone (e.g., gaseous NO) to achieve the same or similar antimicrobial activity and/or reduction in viscosity and/or elasticity of the mucus. In some embodiments, the amount of the NO-releasing biopolymer may be less than the amount of a control compound to achieve the same or similar antimicrobial activity and/or reduction in viscosity and/or elasticity of the mucus.

In some embodiments, a method of the present invention comprises administering a therapeutically effective amount of the NO-releasing biopolymer to a subject. As used herein, the term "therapeutically effective amount" refers to an amount of a NO-releasing biopolymer of the present invention that elicits a therapeutically useful response in a subject. Those skilled in the art will appreciate that the therapeutic effects need not be complete or curative, as long as some benefit is provided to the subject.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the symptom.

In some embodiments, a NO-releasing biopolymer (e.g., NO-releasing polyglucosamine) may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

A method of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject has findings typically associated with, is suspected to have, and/or the subject has an infection and/or cystic fibrosis. A subject "in need of" the methods disclosed herein may be a subject that is experiencing a disease state and/or is anticipated to experience a disease state, and the methods, compounds, and/or compositions of the present invention are used for therapeutic and/or prophylactic treatment of the disease state.

A method of the present invention may deliver and/or administer a NO-releasing biopolymer (e.g., NO-releasing polyglucosamine) of the present invention to mucus that is present in an airway, lungs, bronchi, and/or trachea of a subject. In some embodiments, a method of the present invention delivers and/or administers a NO-releasing biopolymer of the present invention to a mucus plug present in a subject.

A method of the present invention may deliver a NO-releasing biopolymer of the present invention and/or nitric oxide directly to a site of interest (i.e., local delivery). In some embodiments, a method of the present invention delivers a NO-releasing biopolymer of the present invention and/or nitric oxide to a subject and does not produce systemic effects from the administration of nitric oxide. Some embodiments include locally delivering a NO-releasing biopolymer of the present invention and/or nitric oxide to a subject (e.g., targeted delivery to an area in the subject) without providing systemic exposure and/or a toxic effect to other areas of the subject that are not targeted.

A method of the present invention may administer nitric oxide at a therapeutic dose that is lower than a therapeutic dose of nitric oxide alone and/or for a control compound. Thus, by administering a NO-releasing biopolymer of the present invention, nitric oxide may be delivered and/or administered at a dose that is therapeutically effective and lower than a dose of nitric oxide alone and/or for a control compound to achieve the same or similar therapeutic effect. In some embodiments, a method of the present invention may administer and/or deliver nitric oxide at a dose to achieve a therapeutic effect that this at least 10% less than the dose of nitric oxide alone and/or for a control compound to achieve the same or similar therapeutic effect.

A method of the present invention may administer a NO-releasing biopolymer of the present invention to a subject and/or mucus 1 or more times (e.g., 1, 2, 3, 4, or more times) a day, every day, every other day, every 3, 4, 5, or 6 days, or once a week. In some embodiments, the NO-releasing biopolymer may be administered to a subject and/or mucus 1, 2 or 3 times a day for 1, 2, 3, or 4 weeks. A method of the present invention administers a NO-releasing biopolymer of the present invention to a subject and/or mucus 1 or more times during a treatment period. A "treatment period" as used herein refers to the time period from a first administration and/or dose of a NO-releasing biopolymer of the present invention to a last administration and/or dose of a NO-releasing biopolymer of the present invention. The treatment period may be 1 or more day(s) or week(s).

In some embodiments, a NO-releasing biopolymer of the present invention may be administered to a subject and/or mucus at least once daily for a treatment period of 1, 2, 3, 4, 5, 6, 7, 8, 9, 10, 15, 20, 25, 30, 35, 40, 45, 50, or more day(s) or week(s), or any range and/or individual value therein. In some embodiments, a NO-releasing biopolymer of the present invention may be administered to a subject and/or mucus at least once daily for a treatment period of less than 50 day(s) or week(s), e.g., less than 48, 45, 40, 35, 30, 25, 20, 15, 12, 10, 6, 4, 3, or 2 day(s) or week(s), or any range and/or individual value therein. In some embodiments, following one or more administrations and/or doses of the NO-releasing biopolymer to the subject and/or mucus, modifications in one or more physical and/or biophysical properties of mucus may be achieved and/or one or more pathogens may be killed and/or their growth inhibited. In some embodiments, a single administration and/or dose achieves one or more modifications in a physical and/or biophysical property of mucus and/or one or more pathogens may be killed and/or their growth inhibited. In some embodiments, two or more (e.g., 2, 3, 4, 5, or more) administrations and/or doses achieves one or more modifications in a physical and/or biophysical property of mucus and/or one or more pathogens may be killed and/or their growth inhibited. In some embodiments, a method of the present invention achieves one or more modifications in a physical and/or biophysical property of mucus and/or one or more pathogens may be killed and/or their growth inhibited at the end of a treatment period (e.g., within about 24 hours of the last administration and/or dose of the NO-releasing biopolymer).

In some embodiments, a NO-releasing biopolymer (e.g., NO-releasing polyglucosamine) of the present invention is contacted to mucus at a concentration of about 0.1 mg to about 100 mg of the NO-releasing biopolymer per mL of mucus. In some embodiments, the NO-releasing biopolymer may be administered at a dosage such that the NO-releasing biopolymer is present at a concentration of about 0.1 mg to about 100 mg of the NO-releasing biopolymer per mL of mucus. The NO-releasing biopolymer may be contacted to mucus and/or administered to a subject a concentration of about 0.1, 0.5, 1, 5, 10, 15, 20, 25, 30, 35, 40, 45, 50, 55, 60, 65, 70, 75, 80, 85, 90, 95, or 100 mg of the NO-releasing biopolymer per mL of mucus, or any range comprising any two individual values therein.

In some embodiments, a NO-releasing biopolymer may be contacted to mucus and/or administered to a subject at a concentration effective to kill a pathogen. A method of the present invention may administer a NO-releasing biopolymer of the present invention and/or deliver nitric oxide in an amount to provide a one, two, or three log reduction in the numbers of the pathogen. A one-log reduction represents a 10-fold (i.e., $10^1$) or 10% drop in the number. A two-log reduction represents a 100-fold (i.e., $10^2$) or 99% drop in the number. A three-log reduction represents a 1000-fold (i.e., $10^3$) or 99.9% drop in the number. The reduction in the numbers of the pathogen may be measured at a time point after one or more (e.g., 1, 2, 3, 4, 5 or more) administrations of the NO-releasing biopolymer (e.g., at the end of a treatment period).

In some embodiments, the NO-releasing biopolymer may be contacted to mucus and/or administered to a subject at a concentration of about 0.1 mg to about 20 or 40 mg of the NO-releasing biopolymer per mL of solution in which the pathogen is present and that provides at least a one, two, or three log reduction in numbers of the pathogen. In some embodiments, a method of the present invention may administer a NO-releasing biopolymer of the present invention and/or deliver nitric oxide in an amount that is less than the amount needed for an antibiotic to provide a one, two, or three log reduction in the numbers of the pathogen.

A NO-releasing biopolymer (e.g., NO-releasing polyglucosamine) may be administered to a subject and/or contacted to mucus at a weight ratio of about 1:3, 1:2, 1:1, 2:1, 3:1, 4:1, 5:1, 6:1, or 7:1 (NO-releasing biopolymer:mucin). For example, in some embodiments, a mucin may be present in an amount of about 6.5 mg/mL of mucus and a NO-releasing biopolymer may be administered in an amount of about 10 mg/mL of mucus, so that the NO-releasing biopolymer is administered to the subject in a weight ratio in a range of about 2:1 to about 1:1. In some embodiments, the NO-releasing biopolymer is administered to the subject in a weight ratio in a range of about 4:1 to about 2:1, or about 7:1 to about 1:3.

A NO-releasing biopolymer (e.g., NO-releasing polyglucosamine) of the present invention may release nitric oxide in an amount of at least about 0.1 μmol of nitric oxide per mg of the NO-releasing biopolymer as measured in vitro via chemiluminescence with 1.0 mg of the NO-releasing biopolymer in 30 mL of deoxygenated phosphate buffered saline (pH 6.5 or 7.4) at 37° C. with analysis terminated when NO concentrations are below 10 ppb NO/mg of the NO-releasing biopolymer. In some embodiments, a NO-releasing biopolymer of the present invention may release nitric oxide in an amount of about 0.1 μmol to about 1 or 2 μmol of nitric oxide per mg of the NO-releasing biopolymer as measured in vitro via chemiluminescence with 1.0 mg of the NO-releasing biopolymer in 30 mL of deoxygenated phosphate buffered saline (pH 6.5 or 7.4) at 37° C. with analysis terminated when NO concentrations are below 10 ppb NO/mg of the NO-releasing biopolymer. In some embodiments, a NO-releasing biopolymer of the present invention may release nitric oxide in an amount of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 μmol of nitric oxide per mg of the NO-releasing biopolymer as measured in vitro via chemiluminescence as described herein, or any range comprising any two individual values therein.

A NO-releasing biopolymer of the prevention invention may have a half-life of about 15 minutes to about 8 hours such as, e.g., of about 15 minutes to about 45 minutes, about 1 hour to about 8 hours, or 4 hours to about 6 hours, as measured in vitro via chemiluminescence as described herein. In some embodiments, a NO-releasing biopolymer of the present invention may have a half-life of about 15, 30, 45, or 60 minutes, or about 1.5, 2, 2.5, 3, 3.5, 4, 4.5, 5, 5.5, 6, 6.5, 7, 7.5, or 8 hours as measured in vitro via chemiluminescence as described herein.

In some embodiments, a NO-releasing biopolymer of the prevention invention may release nitric oxide at a concentration above 10 ppb NO/mg of the NO-releasing biopolymer for at least about 4 hours as measured in vitro via chemiluminescence as described herein, such as, e.g., at least about 6, 7, 8, 9, 10, 11, 12, 13, 14, 15, 16, 17, 18, 19, 20, 21, 22, 23, or 24 hours as measured in vitro via chemiluminescence as described herein. In some embodiments, a NO-releasing biopolymer of the prevention invention may release nitric oxide at a concentration above 10 ppb NO/mg of the NO-releasing biopolymer for about 4 hours to about 24 hours, about 10 hours to about 22 hours, about 6 hours to about 15 hours, about 12 hours to about 20 hours, or about 19 hours to about 20 hours as measured in vitro via chemiluminescence as described herein.

A NO-releasing biopolymer of the prevention invention may have a molecular weight of about 10 kDa or less, such as, for example, about 10, 9.5, 9, 8.5, 8, 7.5, 7, 6.5, 6, 5.5, 5, 4.5, 4, 3.5, 3, 2.5, 2, 1.5, 1, or 0.5 kDa.

In some embodiments, a NO-releasing biopolymer and/or method of the present invention may provide antimicrobial properties and/or may decrease the viscoelasticity of CF sputum, such effects which are not limited to, but may include, reducing mucin size and/or damaging the three-dimensional mucin network. While inhalation of NO gas has been proposed as a mucolytic therapy previously, the subject matter disclosed herein establishes benefits of NO release from a NO-releasing biopolymer of the present invention, such as, e.g., for direct delivery into a mucus plug. In some embodiments, the mucoadhesive properties of the NO-releasing chitosan oligosaccharide scaffolds may enhance NO's potency. The ability to target NO release to mucus, such as, e.g., CF mucus may lower the required NO dose for therapeutic action while simultaneously lessening any potential effects on other NO-mediated processes. In some embodiments, the chitosan oligosaccharides described herein may possess the dual-action potential of NO-releasing chitosan oligosaccharides as antibacterial and mucolytic agents, and may be used, for example, for the treatment of respiratory diseases and/or infections.

In some embodiments, a method of the present invention may treat CF. A NO-releasing biopolymer and/or method of the present invention may degrade mucin produced by human bronchial epithelial cells and/or present in clinical sputum samples, such as, for example, samples collected from patients with cystic fibrosis (CF).

The presently disclosed NO-releasing biopolymers (e.g., NO-releasing polyglucosamines) may be water soluble and/or tunable. These properties may contribute to the usefulness of the presently disclosed NO-releasing biopolymers, such as, for example, in therapeutics and/or disease states where water soluble therapeutics are advantageous, for example, in the treatment of cystic fibrosis. In some embodiments, a NO-releasing biopolymer of the present invention is a polyglucosamine as described in U.S. Patent Application Publication No. 2015/0225488, the disclosure of which is incorporated herein by reference in its entirety.

In some embodiments, a NO-releasing biopolymer can readily penetrate and eradicate biofilms. The terms "disrupting" and "eradicating" refer to the ability of the presently disclosed NO-releasing biopolymers to combat biofilms. The biofilms may be partially eradicated or disrupted, meaning that the cells no longer attach to one another or to a surface. The biofilm may be completely eradicated, meaning that the biofilm is no longer an interconnected, cohesive or continuous network of cells to a substantial degree.

In some embodiments are methods of disrupting, eradicating or preventing a biofilm, such as, e.g., a biofilm a subject. The method may comprise contacting a surface or area that contains a biofilm or is susceptible to a biofilm forming or occupying some or all of the surface or area with a NO-releasing biopolymer of the present invention. The term "biofilm" is intended to mean an aggregate of one or more microorganisms in which cells adhere to each other, usually on a surface. Most any free-floating microorganisms can form a biofilm and/or attach to a surface. Microorganisms can adhere to a surface or each other through weak, reversible adhesion via van der Waals forces. The microorganisms can more permanently anchor using cell adhesion or structures such as pili.

As used herein, the term "water soluble" in reference to a NO-releasing biopolymer of the present invention means that the NO-releasing biopolymer is soluble in water at room temperature at a concentration of greater than about 50, 75, 100, 150, or 200 mg/ml. In some embodiments, water soluble biopolymers (e.g., polyglucosamines) disclosed herein are soluble such that greater than 50 mg of biopolymer dissolves per mL of water at room temperature. In some embodiments, water soluble biopolymers (e.g., polyglucosamines) disclosed herein are soluble such that greater than 75 mg of biopolymer dissolves per mL of water at room temperature. In some embodiments, water soluble biopolymers (e.g., polyglucosamines) disclosed herein are soluble such that greater than 100 mg of biopolymer dissolves per mL of water at room temperature. In some embodiments, water soluble biopolymers (e.g., polyglucosamines) disclosed herein are soluble such that greater than 150 mg of biopolymer dissolves per mL of water at room temperature. In some embodiments, water soluble biopolymers (e.g., polyglucosamines) disclosed herein are soluble such that greater than 200 mg of biopolymer dissolves per mL of water at room temperature.

The terms "nitric oxide donor" or "NO donor" refer to species that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The terms "nitric oxide releasing" or "nitric oxide donating" refer to methods of donating, releasing and/or directly or indirectly transferring any of the three redox forms of nitrogen monoxide ($NO+$, $NO^-$, NO). In some cases, the nitric oxide releasing or donating is accomplished such that the biological activity of the nitrogen monoxide species is expressed at the intended site of action.

In some embodiments, the oligosaccharides described herein are polyglucosamines. Polyglucosamines and derivatives thereof are known as chitosans and derivatives thereof. Particularly useful polyglucosamines are polymers that can range in size 1000 g/mol to 20,000 g/mol. Smaller polyglucosamines having molecular weights below 1000 g/mol and larger ones having molecular weights above 20,000 g/mol are also contemplated. Chitosans having a molecular weight above 20,000 g/mol may need to be further functionalized to be water soluble. An important feature of useful polyglucosamines is an available nitrogen on the carbohydrate backbone and/or pendant therefrom that is derivatized according to the methods described herein to form a NO-releasing polyglucosamine. Advantageously, the polyglucosamines disclosed herein are water soluble.

Chitosan is a linear polysaccharide composed of randomly distributed β-(1-4)-linked D-glucosamine (deacetylated unit) and N-acetyl-D-glucosamine (acetylated unit). It is a polyglucosamine. Chitosan is derived from chitin, a polysaccharide found in the exoskeleton of shellfish such as shrimp, lobster, crabs, or from fungal sources. It has the following structure:

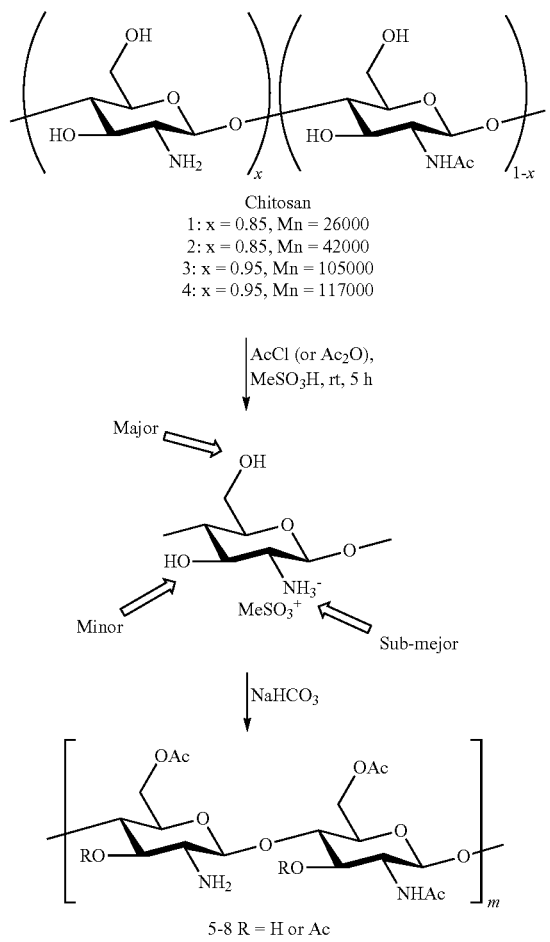

Chitosan is biodegradable and biocompatible. High molecular weight chitosan has limited solubility and is more soluble under acidic conditions. Chitosan polysaccharides having molecular weights greater than about 20,000 g/mol exhibit limited aqueous solubility under physiological conditions. Additionally, the high molecular weight chitosan may exhibit limited NO storage (~0.2 μmol/mg), likely due to poor solubility of polysaccharides in basic solutions necessary for NO donor formation. Valmikinathan, C. M.; Mukhatyar, V. J.; Jain, A.; Karumbaiah, L.; Dasari, M.; Bellamkonda, R. V. Photocrosslinkable chitosan based hydrogels for neural tissue engineering. *Soft Matter* 2012, 8, 1964-1976; Zhang, J. L.; Xia, W. S.; Liu, P.; Cheng, Q. Y.; Tahirou, T.; Gu, W. X.; Li, B. Chitosan Modification and Pharmaceutical/Biomedical Applications. *Mar. Drugs* 2010, 8, 1962-1987; Wan, A.; Gao, Q.; Li, H. L. Effects of molecular weight and degree of acetylation on the release of nitric oxide from chitosan-nitric oxide adducts. *J. Appl. Polym. Sci.* 2010, 117, 2183-2188. To synthesize N-diazeniumdiolate-functionalized chitosan derivatives with improved NO storage, we prepared water-soluble chitosan oligosaccharides by the degradation of chitosan polysaccharides in hydrogen peroxide. A benefit of the chitosan oligosaccharides described herein are relatively low-molecular weight from 1000 to 20,000 g/mol, in particular about 10,000 g/mol or less; or about 8000 g/mol or less; or about 5000 g/mol or less; or about 2,500 g/mol or less and their ability to readily penetrate biofilms. Maghami, G. G.; Roberts, G. A. F. Evaluation of the viscometric constants for chitosan. *Makromol. Chem.* 1988, 189, 195-200; Porporatto, C.; Bianco, I. D.; Riera, C. M.; Correa, S. G., Chitosan induces different L-arginine metabolic pathways in resting and inflammatory macrophages. *Biochem. Biophy. Res. Comm.* 2003, 304, 266-272. Chitosan oligosaccharides described herein have greater NO storage of up to about 8.7 μmol/mg and are also soluble under neutral and basic conditions.

The primary amino groups on the backbone of chitosan are chemical handles for the preparation of the NO-releasing oligosaccharides disclosed herein. As shown in the schemes below, secondary amino groups are prepared from the primary amino groups.

One exemplary agent useful to form the secondary amino groups are aziridines, for example, 2-methyl aziridine. Thiiranes and the like may be used in addition to other synthetic schemes as known now or which may become known in the art.

As described herein, a polyglucosamine comprises at least one structure unit of Formula I. In some embodiments, $R_1$, $R_2$, $R_3$ and $R_4$, if present, are each independently selected from the group consisting of hydrogen and $C_{1-5}$ alkyl. When one or more of $R_1$, $R_2$, $R_3$ and $R_4$ is $C_{1-5}$ alkyl, it may be selected from methyl, ethyl, n-propyl, isopropyl, t-butyl, n-butyl, isobutyl and pentyl. In some embodiments, $R_1$, $R_2$, $R_3$ and $R_4$, if present, are hydrogen or methyl. In some embodiments, $R_1$, $R_2$, $R^3$ and $R_4$, if present, are hydrogen.

In some embodiments, ≈ is a single bond in all instances.

In some embodiments, W is -(Q-A)$_p$-B and Q is —(CR$_c$R$_d$)$_v$—; wherein R$_c$ and R$_d$ are, in each instance, independently hydrogen or $C_{1-5}$ alkyl, such as methyl, ethyl, n-propyl, isopropyl, t-butyl, n-butyl, isobutyl and pentyl. In some embodiments, R$_c$ and R$_d$ are, in each instance, independently hydrogen, methyl or ethyl. In some embodiments, v is 1 or 2.

Useful values of p include any integer from 1 to 100. In some embodiments, p is an integer from 1 to 50. In some embodiments, p is an integer from 1 to 25. In some embodiments, p is an integer from 1 to 10, such as, 1, 2, 3, 4, 5, 6, 7, 8, 9 and 10.

In some embodiments, W is -Q-A-B. In some embodiments, W is —$C_{1-20}$ alkyl-A-B. A $C_{1-20}$ alkyl may refer to a straight or branched chain hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, a $C_{1-20}$ alkyl may comprise a repeating alkyl unit, such as, but not limited to, —($CH_2CH_2$)$_{1-10}$—, —($CH(CH_3)CH_2$)$_{1-9}$— or —($CH_2CH(CH_3)$)$_{1-9}$—.

In some embodiments, L is N or S. In each instance that G occurs, it is independently hydrogen or a nitric oxide donor. In some embodiments, G is a nitric oxide donor. In some embodiments, at least 30% of G present on a polyglucosamine is a nitric oxide donor. In some embodiments, at least 50% of G present on a polyglucosamine is a nitric oxide donor. In some embodiments, at least 90% of G present on a polyglucosamine is a nitric oxide donor. In some embodiments, at least 95% of G present on a polyglucosamine is a nitric oxide donor.

In some embodiments, X is a nitric oxide donor. In some embodiments, at least 30% of X present on a polyglucosamine is a nitric oxide donor. In some embodiments, at least 50% of X present on a polyglucosamine is a nitric oxide donor. In some embodiments, at least 90% of X present on a polyglucosamine is a nitric oxide donor. In some embodiments, at least 95% of X present on a polyglucosamine is a nitric oxide donor.

In some embodiments, B is hydrogen or —Y—Z, wherein Y is a spacer and Z is a monomer or polymer, or a terminus group. In some embodiments, B is absent, such as, e.g., when L is O or S. As used herein, a terminus group is any end-capping group at the terminus of a polymer or monomer. These groups are known in the art. In some embodiments, when B is a terminus group, it is hydrogen, hydroxyl or $C_{1-5}$ alkyl.

In some embodiments, B is a $C_{1-20}$ alkyl as described. In some embodiments, B is a $C_{1-20}$ alkyl.

In some embodiments, Z is a monomer or polymer known in the art, especially those used in active pharmaceutical ingredients. In some embodiments, Z is a $C_{1-20}$ alkyl as described. In some embodiments, Z has one of the following structures:

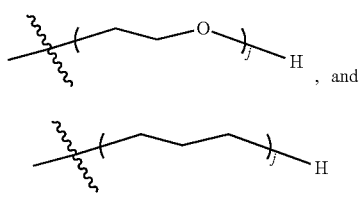

, and

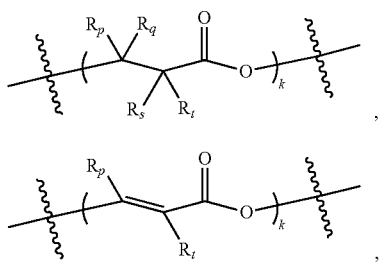

wherein j, in each instance, is an integer from 1 to 100.

In some embodiments, Y is a spacer or linker known in the art, especially those used in active pharmaceutical ingredients. In some embodiments, Y is $C_{1-6}$ alkyl or has one of the following structures:

iii iv

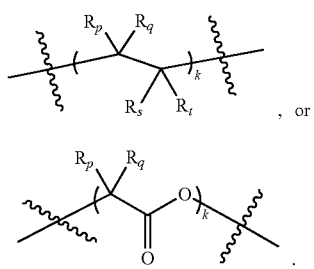

, or vi wherein, $R_p$, $R_q$, $R_s$ and $R_t$, in each instance, are independently, hydrogen or hydroxyl; and k is an integer from 1 to 20.

Using the strategies disclosed herein, any secondary amino group present on the polyglucosamine can be modified as described herein to form a NO-releasing polyglucosamine. The secondary amino groups attached directly to the sugar backbone moieties or secondary amino groups pendant on the backbone sugar moieties can be functionalized with a NO releasing moiety. As disclosed fully herein in the synthetic routes, primary amines are modified to secondary amines. This modification can be facilitated by aziridines, thiiranes and the like.

Useful NO releasing moieties include any NO releasing group known in the art. Particularly useful are residues of NO releasing groups, i.e. NO donors, are covalently bound to N on the polyglucosamine. The NO donor is taken together with the atom on the polyglucosamine to which it is bound to form a moiety selected from the group consisting of a diazeniumdiolate, —NO as part of a nitrosothiol group for example, a nitrosamine, a hydroxyl nitrosamine, a hydroxyl amine, a hydroxyurea, and combination thereof. In some embodiments, the NO releasing moiety is a diazeniumdiolate. These groups may be present in the form of a salt.

In some embodiments, the NO donor is a N-diazeniumdiolate (i.e., a 1-amino-substituted deazen-1-lum-1,2-diolate), N-Diazeniumdiolates are particularly attractive as NO donors due to their ability to generate NO spontaneously under biological conditions. See Hrabie, J. A. and Keefer, L. K., Chem. Rev., 102, 1135-1154 (2002); and Napoli, C. and Lanarro, L. J., Annu. Rev. Pharmacol. Toxicol., 43, 97-123 (2003). Several N-diazeniumdiolate compounds have been synthesized using a range of nucleophilic residues that encompass primary and secondary amines, polyamines, and secondary amino acids, See Hrabie, J. A., and Keefer L. K., Chem. Rev., 102, 1135-1154 (2002). In the formation of the N-diazeniumdiolate, one equivalent of amine reacts with two equivalents of nitric oxide under elevated pressure. A base (e.g., an alkoxide like methoxide) removes a proton from the amine nitrogen to create the anionic, stabilized [N(O)NO] group. While stable under ambient conditions, N-diazeniumdiolates decompose spontaneously in aqueous media to generate NO at rates dependent upon pH, temperature, and/or the structure of the amine moiety. For example, N-diazeniumdiolate-modified proline (PROLI/NO), 2-(dimethylamino)-ethylputreamlne (DMAEP/NO), N,N-dimethylhexanediamine (DMHD/NO), and diethylenetriamine (DETA/NO) have been developed as small molecule NO donors with diverse NO release half-lives ranging from 2 seconds to 20 hours at pH 7.4 and 37° C. See Hrabie, J. A., and Keefer, L. K., Chem. Rev., 102, 1135-1154 (2002); and Keefer, L. K., Annu, Rev. Pharmacol. Toxicol 43, 585-607 (2003).

The secondary amine functional group of the polyglucosamine is converted in high yields to a nitric oxide donor in the presence of a strong base and gaseous nitric oxide. The solvent system can affect the charging of the polyglucosamine with NO.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

The terms "cationic amine" and "quaternary amine" refer to an amino group having an additional (i.e., a fourth) group, for example, a hydrogen or an alkyl group bonded to the nitrogen. Thus, cationic and quaternary amines carry a positive charge.

The term "alkyl" denotes a straight or branched hydrocarbon chain containing 1-24 carbon atoms, e.g., 1-12 carbon atoms. Examples of alkyl group include methyl, ethyl, propyl, isopropyl, butyl, isobutyl, tert-butyl, and the like.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. In some embodiments, the alkoxy chain is 1 to 5 carbon atoms in length or 1-3 carbon atoms in length.

For subject matter covering charged species, the charged species may have a counter ion. The counter ion may be any organic or inorganic moiety that stabilizes the charge on the parent compound. Furthermore, a charged species may have more than one charged atom in its structure. Instances where multiple charged atoms are part of the charged species, the salt can have multiple counter ions. Hence, a charged species can have one or more charged atoms and/or one or more counter ion. Non-limiting examples of inorganic counter ions are Na, K, Cs, Mg, Ca, and the like.

In all embodiments, combinations of substituents and/or variables are permissible only if such combinations result in compounds that conform to a known valence for each atom.

According to some embodiments of the present invention is a method of delivering nitric oxide to a subject, comprising administering a NO-releasing biopolymer (e.g., NO-releasing polyglucosamine) of the present invention to the subject.

In some embodiments, a method of treating a disease state is provided, the method comprising administering an effective amount of a NO-releasing biopolymer of the present invention to a subject in need thereof. As used herein, the term "disease state" refers to any abnormal condition that interferes with a physiological process. Non-limiting disease states are listed herein and more than one disease state (i.e., multiple disease states) may be present in a subject at the same time. In some embodiments, treatment of multiple disease states may occur in a concomitant manner, such that the multiple disease states are treated simultaneously. For example, disease states include, but are not limited to, a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, sexually transmitted diseases, and combinations thereof.

The term "microbial infection" as used herein refers to a bacterial, fungal, viral, and/or yeast infection.

As used herein, the term "respiratory disorder" refers to any condition or disease related to respiration or the respiratory system and includes, but is not limited to, airway inflammation, asthma, emphysema, bronchitis, COPD, sinusitis, rhinitis, cough, bronchospasm, airflow obstruction, exercise-induced bronchospasm, exacerbations, bronchoconstriction, respiratory depression, reactive airways dysfunction syndrome (RADS), acute respiratory distress syndrome (ARDS), irritant induced asthma, occupational asthma, sensory hyper-reactivity, multiple chemical sensitivity, and cystic fibrosis.

In some embodiments, the disease state is cystic fibrosis. In some embodiments, the disease state is a microbial infection. In some embodiments, the disease state is cystic fibrosis and a microbial infection.

Provided according to some embodiments of the present invention is a pharmaceutical formulation comprising: a NO-releasing biopolymer of the present invention and a pharmaceutically acceptable carrier.

"Pharmaceutically acceptable," as used herein, means a material that is not biologically or otherwise undesirable, i.e., the material can be administered to an individual, along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 20 ed. 2005). Exemplary pharmaceutically acceptable carriers for the compositions of this invention include, but are not limited to, sterile pyrogen-free water and sterile pyrogen-free physiological saline solution.

Compositions of the present invention may comprise a NO-releasing biopolymer of the present invention and a pharmaceutically acceptable carrier. Suitable compositions include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions used in the presently disclosed methods can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

The compositions can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds also can be formulated in rectal compositions (e.g., suppositories or retention enemas containing conventional suppository bases, such as cocoa butter or other glycerides), creams or lotions, or transdermal patches.

Pharmaceutical formulations also are provided which are suitable for administration as an aerosol by inhalation. In some embodiments, the NO-releasing biopolymers described herein are formulated in solution and/or aerosol form. These formulations comprise a solution or suspension of a NO-releasing biopolymer described herein. The desired formulation can be placed in a small chamber and nebulized. Nebulization can be accomplished by compressed air or by ultrasonic energy to form a plurality of liquid droplets or solid particles comprising the NO-releasing biopolymer. For example, the presently disclosed NO-releasing biopolymer can be administered via inhalation to treat bacterial infections related to cystic fibrosis. Cystic fibrosis-related bacterial infections include, but are not limited to *stenotrophomonis, Myobacterium avium intracellulaire* and *M. abcessus, Burkhoderia cepacia* and *Pseudomonas aeruginosa* (*P. aeruginosa*) infections.

The term "effective amount" is used herein to refer to an amount of a NO-releasing biopolymer and/or composition of the present invention sufficient to produce a measurable biological response. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors, including the activity of the composition, formulation, the route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12. (Freireich et al., *Cancer Chemother Rep.* 50, 219-244 (1966)). Drug doses also can be given in milligrams per square meter of body surface area because this method, rather than body weight, achieves a good correlation to certain metabolic and excretionary functions. Moreover, body surface area can be used as a common denominator for drug dosage in adults and children, as well as in different animal species. (Freireich et al., *Cancer Chemother Rep.* 50, 219-244 (1966)). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For additional guidance regarding formulation and dose, see U.S. Pat. Nos. 5,326,902; 5,234,933; PCT International Publication No. WO 93/25521; Berkow et al., The Merck Manual of Medical Information, Home ed., Merck Research Laboratories: Whitehouse Station, N.J. (1997); Goodman et al., *Goodman & Gilman's the Pharmacological Basis of Therapeutics,* 9th ed. McGraw-Hill Health Professions Division: New York (1996); Ebadi, *CRC Desk Reference of Clinical Pharmacology*, CRC Press, Boca Raton, Fla. (1998); Katzunq, *Basic & Clinical Pharmacology,* 8th ed. Lange Medical Books/McGraw-Hill Medical Pub. Division: New York (2001); Remington et al., *Remington's Pharmaceutical Sciences,* 15th ed. Mack Pub. Co.: Easton, Pa. (1975); and Speight et al., *Avery's Drug Treatment: A Guide to the Properties, Choice, Therapeutic Use and Economic Value of Drugs in Disease Management,* 4th ed. Adis International: Auckland/Philadelphia (1997); Dutch et al., *Toxicol. Leu.,* 100-101, 255-263 (1998).

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

In some embodiments, one or more additional therapeutic agents can be used in combination with the NO-releasing biopolymer. Such additional agents can be part of a formulation comprising the NO-releasing biopolymer or dosed as a separate formulation prior to, after, or at the same time (concurrently) as a formulation including the NO-releasing biopolymer. Such additional therapeutic agents include, in particular, anti-cancer therapeutics, anti-microbial agents, pain relievers, anti-inflammatories, vasodialators, and immune-suppressants, as well as any other known therapeutic agent that could enhance the alleviation of the disease or condition being treated. "Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time, but at different anatomic sites or using different routes of administration.

The choice of additional therapeutic agents to be used in combination with an NO-releasing biopolymer will depend on various factors including, but not limited to, the type of disease, the age and general health of the subject, the aggressiveness of disease progression, and the ability of the subject to tolerate the agents that comprise the combination.

A variety of chemical compounds, also described as "antineoplastic" agents or "chemotherapeutic agents" can be used in combination with the presently disclosed NO-releasing biopolymers used in the treatment of cancer. Such chemotherapeutic compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, can be used as part of the presently disclosed cancer treatments. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, a-amanitine and other fungal amatoxins, cordycepin (3'-deoxyadenosine), dichlororibofuranosyl benzimidazole, rifampicine, streptovaricin, and streptolydigin also can be combined with the NO-releasing biopolymers to provide a suitable cancer treatment.

Thus, current chemotherapeutic agents that can be used in combination with the presently described NO-releasing biopolymers include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chjlorambucil, bisulfan, nitrosurea, dactinomycin, duanorubicin, doxorubicin, bleomycin, pilcomycin, tamoxifen, taxol, transplatimun, vinblastin, and methotrexate, and the like.

As used herein, the term "antimicrobial agent" refers to any agent that kills, inhibits the growth of, or prevents the growth of a bacteria, fungus, yeast, or virus. Suitable antimicrobial agents that can be incorporated into the presently disclosed NO-releasing biopolymers to aid in the treatment or prevention of a microbial infection, include, but are not limited to, antibiotics such as vancomycin, bleomycin, pentostatin, mitoxantrone, mitomycin, dactinomycin, plicamycin and amikacin. Other antimicrobial agents include antibacterial agents such as 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefininox, cefodizime, cefonicid, cefoperazone, cefuranide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clindamycin phosphate, clomocycline, colistin, cyclacillin, dapsone, demecicycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilyl-benzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin and vancomycin. Antimicrobial agents can also include anti-fungals, such as amphotericin B, azaserine, candicidin(s), chlorphenesin, dermostatin(s), filipin, fungichromin, mepartricin, nystatin, oligomycin(s), perimycin A, tubercidin, imidazoles, triazoles, and griesofulvin.

In some embodiments, the NO-releasing biopolymer can be incorporated into polymeric films. Such incorporation can be through physically embedding the NO-releasing biopolymer into polymer surfaces, via electrostatic association of the NO-releasing biopolymer onto polymeric surfaces, or by covalent attachment of NO-releasing biopolymer onto reactive groups on the surface of a polymer. Alternatively, the NO-releasing biopolymer can be mixed into a solution of liquid polymer precursor, becoming entrapped in the polymer matrix when the polymer is cured. Polymerizable groups can also be used to further functionalize the NO-releasing biopolymer, whereupon, the NO-releasing biopolymer can be co-polymerized into a polymer during the polymerization process. Suitable polymers into which the NO-releasing biopolymer can be incorporated include polyolefins, such as polystyrene, polypropylene, polyethylene, polytetrafluoroethylene, and polyvinylidene, as well as polyesters, polyethers, polyurethanes, and the like. In particular, polyurethanes can include medically segmented polyurethanes. Medically segmented polyurethanes can also include one or more expander moieties, such as alkylene chains that add additional length or weight to the polymer. Such polyurethanes are also generally non-toxic. One example of a medically segmented polyurethane is TECOFLEX®.

Polymeric films containing NO-releasing biopolymers can be used to coat a variety of articles, particularly surgical tools, biological sensors, and medical implants to prevent platelet adhesion, to prevent bacterial infection, or to act as a vasodilator. These articles can be of use in vascular medical devices, urological medical devices, biliary medical devices, gastrointestinal medical devices, medical devices adapted for placement at surgical sites, and medical devices adapted for placement on skin wounds or openings. Thus, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

In some embodiments, the device being coated can have a metallic surface, such as, for example, stainless steel, nickel, titanium, aluminum, copper, gold, silver, platinum, and combinations thereof. In some embodiments, the films or polymers containing the NO-releasing biopolymer can be used to coat non-metallic surfaces, such as glass or fiber (e.g., cloth or paper).

Additionally, polymers containing NO-releasing biopolymers can be used to form the devices themselves. For example, the polymers can be fashioned into storage bags for blood or tissue or as wound dressings.

Surfaces that can be contacted with a NO-releasing biopolymer to prevent or disrupt biofilms include those selected from the group consisting of medical devices, plumbing fixtures, condenser coils, optical surfaces, boat hulls and aircrafts. Other non-limiting examples include counter tops, windows, appliances, hard floors, rugs, tubs, showers, mirrors, toilets, bidets, bathroom fixtures, sinks, refrigerators, microwaves, small kitchen appliances, tables, chairs, cabinets, drawers, sofas, love seats, benches, beds, stools, armoires, chests, dressers, display cabinets, clocks, buffets, shades, shutters, entertainment centers, arm rails, lamps, banisters, libraries, cabinets, desks, doors, shelves, couches, carts, pianos, statues and other art, racks, fans, light fixtures, pool tables, ping pong tables, soccer tables, card tables, tools (e.g., hand powered and/or hand held tools, electrical tools, air powered tools, etc.), telephones, radios, televisions, stereo equipment, CD and DVD players, analog and digital sound devices, palm computers, laptop computers, desktop and tower computers, computer monitors, mp3 players, memory storage devices, cameras, camcorders, vehicle surfaces (e.g., windshield; tires; metal, fiberglass, composite material and/or plastic outer surfaces; fabric and/or vinyl outer surfaces; fabric, vinyl, and/or leather interior surfaces; metal, plastic, wood and/or composite material interior surfaces, glass interior surfaces, etc.), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. Any surface where it is desirable to cause one or more types of liquids to run off of a surface, to not be absorbed into a surface, and/or to not stain a surface, can be a substrate. For example, the surface may be a surface that is exposed to environmental conditions. In further embodiments, the surface may be one which can become a locus for microbial adhesion such as medical devices that contact bodily tissues or fluids.

Medical devices such as catheters, which are adapted for movement through blood vessels or other body lumens, are typically provided with low-friction outer surfaces. If the surfaces of the medical devices are not low-friction surfaces, insertion of the devices into and removal of the devices from the body lumens becomes more difficult, and injury or inflammation of bodily tissue may occur. Low friction surfaces are also beneficial for reducing discomfort and injury that may arise as a result of movement between certain long term devices (e.g., long term catheters) and the surrounding tissue, for example, as a result of patient activity. Medical devices include a variety of implantable and insertable medical devices (also referred to herein as "internal medical devices"). Examples of such medical devices include, devices involving the delivery or removal of fluids (e.g., drug containing fluids, pressurized fluids such as inflation fluids, bodily fluids, contrast media, hot or cold media, etc.) as well as devices for insertion into and/or through a wide range of body lumens, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth. Non-limiting, specific examples of internal medical devices include vascular devices such as vascular catheters (e.g., balloon catheters), including balloons and inflation tubing for the same, hydrolyser catheters, guide wires, pullback sheaths, filters (e.g., vena cava filters), left ventricular assist devices, total artificial hearts, injection needles, drug delivery tubing, drainage tubing, gastroenteric and colonoscopic tubing, endoscopic devices, endotracheal devices such as airway tubes, devices for the urinary tract such as urinary catheters and ureteral stents, and devices for the neural region such as catheters and wires, trocar needles, bone anchors, bone screws, protective platings, joint replacements, electrical leads, biosensors, probes, sutures, surgical drapes, wound dressings, and bandages. Many devices in accordance with the invention have one or more portions that are cylindrical in shape, including both solid and hollow cylindrical shapes.

Solid substrate materials can include organic materials (e.g., materials containing 50 wt % or more organic species) such as polymeric materials, and inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others). Specific examples of non-metallic inorganic materials can be materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Further, the NO-releasing biopolymers can be incorporated into detergents, such as, but not limited to, antimicrobial soaps. For example, NO-release from polyglucosamine embedded in bar soaps can be triggered by contact with water and/or a drop in pH upon use. As the outer surface of the bar is eroded or dissolved, additional polyglucosamine within the bar surface become exposed for subsequent uses of the bar. NO-releasing biopolymers also can be suspended in liquid soaps. Such soaps or detergents can be used for personal hygiene or to provide anti-microbial treatments for fibers. Such soaps or detergents can also be used to treat household surfaces or any surface in a hospital or other medical environment that may be exposed to microbes such as bacteria, fungi or viruses.

The term "biocompatible" refers herein to organic solvents that do not induce toxic or unwanted side effects when administered to a patient in certain amounts.

The formulations include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

The NO-releasing biopolymers (e.g., NO-releasing polyglucosamines) also include those having quaternization of any basic nitrogen-containing group therein.

The discussion herein is, for simplicity, provided without reference to stereoisomerism. Those skilled in the art will appreciate that the biopolymers described herein can contain one or more asymmetric centers and thus occur as racemates and racemic mixtures, single optical isomers, individual diastereomers, and diastereomeric mixtures. All such isomeric forms of these compounds are expressly included in the present invention.

Chitosan may possess favorable properties including mucoadhesivity (Grenha, A., et al., *Journal of Drug Delivery Science and Technology*, 20, 33-43 (2010); Dash, M., et al., *Progress in Polymer Science*, 36, 981-1014 (2011)), biodegradability (Grenha, A., et al., *Journal of Drug Delivery Science and Technology*, 20, 33-43 (2010); Kean, T., et al., Adv. *Drug Delivery Rev.*, 62, 3-11 (2010)), and low cytotoxicity (Grenha, A., et al., *Journal of Drug Delivery Science and Technology*, 20, 33-43 (2010)). Electrostatic interactions between chitosan's positively charged amines and the negatively charged sialic acid residues of mucins (Grenha, A., et al., *Journal of Drug Delivery Science and Technology*, 20, 33-43 (2010); Menchicchi, B., et al., *Biomacromolecules*, 15, 3550-3558 (2014); Sogias, I. A., et al., *Biomacromolecules*, 9, 1837-1842 (2008)) is believed to enhance chitosan retention in the airways and therefore increase time of action (Grenha, A., et al., *Journal of Drug Delivery Science and Technology*, 20, 33-43 (2010); Klinger-Strobel, M., et al., *Expert Opinion on Drug Delivery*, 1-24 (2015)). Chitosan has been reported to facilitate delivery and improve efficacy of antibiotic-releasing particles to the lungs (Manca, M.-L., et al., *Colloids and Surfaces B: Biointerfaces*, 62, 220-231 (2008); Park, J.-H., et al., *International Journal of Pharmaceutics*, 441, 562-569 (2013); Jain, D. and Banerjee, R., *Journal of Biomedical Materials Research Part B: Applied Biomaterials*, 86, 105-112 (2008); Osman, R., et al., *International Journal of Pharmaceutics*, 449, 44-58 (2013); Ungaro, F., et al., *Journal of Controlled Release*, 157, 149-159 (2012)). However, mucoadhesion could potentially affect drug penetration into the mucus. Klinger-Strobel et al. described the benefits of modifying chitosan with polyethylene glycol (PEG) (Klinger-Strobel, M., et al., *Expert Opinion on Drug Delivery*, 1-24 (2015)) to facilitate better drug action on human cervicovaginal mucus (Suk, J. S., et al., *Nanomedicine*, 6, 365-375 (2011); Tang, B. C., et al., *Proceedings of the National Academy of Sciences*, 106, 19268-19273 (2009)), bacterial biofilms (Forier, K., et al., *Nanomedicine*, 8, 935-949 (2013)), and CF sputum (Suk, J. S., et al., *Nanomedicine*, 6, 365-375 (2011); Tang, B. C., et al., *P.N.A.S.*, 106, 19268-19273 (2009); Forier, K., et al., *Nanomedicine*, 8, 935-949 (2013); Suk, J. S., et al., *Biomaterials*, 30, 2591-2597 (2009)).

As NO is also a potent antibacterial agent (Reighard, K. P. and Schoenfisch, M. H. *Antimicrobial Agents and Chemotherapy*, 59, 6506-6513 (2015); Reighard, K. P., et al., *Biofouling*, 31, 775-787 (2015); Lu, Y., et al., *Biomaterials*, 35, 1716-1724 (2014); Carpenter, A. W. and Schoenfisch, M. H. *Chemical Society Reviews*, 41, 3742-3752 (2012); Seabra, A. B., et al., *Biotechnology Advances*, 33(6), 1370-1379 (2015); Jones, M. L., et al., *Applied Microbiology and Biotechnology*, 88, 401-407 (2010); Deppisch, C., et al.,

*Infection*, 44(4), 513-520 (2016)), the chitosan oligosaccharides described herein may possess the dual-action potential of NO-releasing chitosan oligosaccharides as antibacterial and mucolytic agents for the treatment of CF. The bactericidal action of NO-releasing chitosan oligosaccharides against CF-relevant *Pseudomonas aeruginosa* in planktonic and biofilm-based cultures has been reported (Reighard, K. P., et al., *Antimicrobial Agents and Chemotherapy*, 59, 6506-6513 (2015); Reighard, K. P., et al., *Biofouling*, 31, 775-787 (2015)). The broad spectrum antibacterial action of nitric oxide makes the subject matter described herein, in certain embodiments, an alternative to traditional antibiotics for which many bacteria have developed resistance.

In some embodiments, the presently disclosed nitric oxide (NO) releasing biopolymers possess antibiotic properties and also decrease the viscoelasticity of CF sputum by reducing mucin size and damaging the three-dimensional mucin network. In other embodiments, the subject matter disclosed herein establishes the benefits of NO release from a mucoadhesive scaffold for direct delivery into the mucus plug. In some embodiments, the mucoadhesive properties of a chitosan oligosaccharide scaffold as described herein can significantly enhance NO's potency. In embodiments, the subject matter disclosed herein can lower the required NO dose for therapeutic action while simultaneously lessening any potential effects on other NO-mediated processes.

In embodiments, the nitric oxide (NO)-releasing chitosan oligosaccharides are modified with acrylate functional groups. In embodiments, the mucoadhesive nature of the scaffold impacts the ability of NO to degrade mucins from human bronchial epithelial cell cultures and clinical sputum samples collected from patients with cystic fibrosis (CF). Agarose gel electrophoresis experiments show that, in certain embodiments, the mucoadhesive NO-releasing chitosan oligosaccharides degraded both the purified mucins and sputum, while control scaffolds (without NO release or mucoadhesive ligands) had no effect on mucin structure. Microscopic observations of sputum treated with certain embodiments of the mucoadhesive NO-releasing chitosan oligosaccharide confirmed degradation of the mucin and DNA networks. In embodiments, the viscosity and elasticity of sputum were reduced upon treatment with the mucoadhesive NO-releasing chitosan, demonstrating the utility of the NO-releasing scaffolds as mucolytic agents.

In embodiments, the presently disclosed nitric oxide (NO) releasing polyglucosamines can be water soluble and tunable. These properties may contribute to the usefulness of the presently disclosed polyglucosamines in therapeutics and disease states where water soluble therapeutics are advantageous, for example, in the treatment of cystic fibrosis. Other advantages over known NO releasing particles that the presently disclosed functionalized NO releasing polyglucosamines may possess include: 1. Distinct synthesis routes and chemical composition by grafting secondary amine-containing side chains onto chitosan oligosaccharides; 2. Tunability of NO storage and NO-release kinetics is an advantage. By tuning the number of secondary amines on the aziridine side chains, NO storage can be controlled. In embodiments, functionalization of the amines on the resulting materials by compounds of different hydrophobicity/hydrophilicity enables the control over NO-release kinetics. In other embodiments, larger NO storage was yielded by the presently disclosed functionalized polyglucosamines; and 3. In contrast to particles, the functionalized polyglucosamines described herein may be water soluble, facilitating a wider range of applications including biomedical application where water-solubility is desired. A previously disclosed NO-releasing chitosan (U.S. Pat. No. 6,451,337) is not water soluble. In other embodiments, the presently disclosed water soluble functionalized oligosaccharides can penetrate and eradicate biofilms.

The present invention is explained in greater detail in the following non-limiting Examples.

EXAMPLES

Example 1

In this study, chitosan oligosaccharides were modified with functional groups that would control mucoadhesive properties while maintaining comparable NO-release characteristics to understand the effects of scaffold mucoadhesion on the mucolytic action of NO.

EXPERIMENTAL

Materials and Methods

Medium molecular weight chitosan (viscosity 200-800 centipoise), 2-methylaziridine, ethyl acrylate, tert-butyl acrylate, sulfopropyl acrylate potassium salt, sodium dodecyl sulfate (SDS), dithiothreitol (DTT), bovine serum albumin (BSA), and type II gastric pig mucin (GPM) were purchased from Sigma-Aldrich (St. Louis, Mo.). Nitric oxide gas was purchased from Praxair (Sanford, N.C.). Argon (Ar), NO calibration (26.85 ppm, balance $N_2$), and nitrogen ($N_2$) gases were purchased from Airgas National Welders (Durham, N.C.). Sodium methoxide was purchased from Acros Organics (Geel, Belgium).

Tris-acetate-EDTA (TAE) buffer (10×) was purchased from Mediatech, Inc. (Manassas, Va.) and diluted 1:10 in distilled water prior to use. Saline-sodium citrate (SSC) buffer (20×) was purchased from Promega Corporation (Madison, Wis.) and diluted 1:5 to obtain 4×SSC buffer. Dulbecco's phosphate buffered saline (DPBS, 1×) was purchase from Life Technologies (Carlsbad, Calif.). Powdered milk (Drink 'n Mix) was purchased from Walmart (Durham, N.C.). Neutral buffered formalin (NBF, 10 vol %) was purchased from Sigma Aldrich (St. Louis, Mo.). Phosphate buffer (10 mM, pH 6.5) and phosphate buffered saline (10 mM, pH 6.5) were prepared in house using common laboratory salts and reagents.

Anti-MUC5B antibody (H-300) was purchased from Santa Cruz Biotechnology (Dallas, Tex.). Anti-MUC5AC antibody (45M1) was purchased from Abcam (Cambridge, Mass.). Secondary antibodies (IRDye 800CW Donkey anti-Mouse IgG and IRDye 680RD Donkey anti-Rabbit IgG) were purchased from LI-COR Biosciences (Lincoln, Nebr.). 4',6-Diamidino-2-phenylindole dihydrochloride (DAPI) was purchased from Life Technologies (Carlsbad, Calif.).

Distilled water was purified using a Millipore Milli-Q UV Gradient A-10 system (Bedford, Mass.). All common laboratory salts and reagents were purchased from Fisher Scientific (Pittsburgh, Pa.). All materials were used without further purification unless specified otherwise.

Culture washings containing mucus were collected from primary human bronchial epithelial (HBE) cell cultures from a patient with CF as previously described (Hill, D. B. and Button, B., "Establishment of respiratory air-liquid interface cultures and their use in studying mucin production, secretion, and function." *Methods Mol. Biol.*, Humana Press, Chpt. 15, pp. 245-258 (2012)). Briefly, primary cell cultures obtained from excess surgical tissue (UNC-Chapel Hill Tissue Core Facility) were grown on 0.5 mm pore-sized Millicell cell culture inserts (Millipore, Bedford, Mass.) in air-liquid interface media (UNC Chapel Hill Tissue Core Facility) for a minimum of 6 weeks until the cultures developed cilia, and well-defined periciliary liquid (PCL) and mucus layers. Washings were collected by adding 150 µL of PBS per 1 cm$^2$ of culture area after 2 d of mucus accumulation. Subsequently, these washings were treated immediately with chitosan oligosaccharides for analysis.

Sputum samples were collected from CF patients by spontaneous expectoration. The samples were stored in sterile containers at −20° C. until use.

Synthesis of 2-Methylaziridine Modified Chitosan Oligosaccharides

Polymeric chitosan was oxidatively degraded into chitosan oligosaccharides as described previously (Lu, Y., et. al., *Biomaterials*, 35, 1716-1724 (2014)). Medium molecular weight chitosan (2.5 g) was dissolved in 15 wt % hydrogen peroxide (50 mL) and stirred at 85° C. for 1 h. Insoluble, non-degraded chitosan was removed by filtration. Water-soluble oligosaccharides were collected via precipitation in acetone, washed copiously with ethanol, and dried in vacuo. An Ubbelohde viscometer was used to measure the viscosity of the chitosan oligosaccharides in a solution of sodium chloride (0.20 M) and acetic acid (0.10 M) at 25° C. The molecular weight was calculated to be 4.41±0.04 kD using the classic Mark-Houwink equation ($q=1.81 \times 10^{-3}$ $M^{0.93}$) (Maghami, G. G. and Roberts, G. A., *Die Makromolekulare Chemie*, 189, 195-200 (2000)).

The water-soluble chitosan oligosaccharides were then modified with 2-methylaziridine (Scheme 1). Chitosan oligosaccharides (0.50 g) were dissolved in stirred water (10.00 mL). Hydrochloric acid (12.1 M, 27.5 µL), water (250 µL), and 2-methylaziridine (178 µL, 1:1 molar ratio to primary amines on the unmodified chitosan oligosaccharide) were then added to this solution, with continuous stirring for 5 d at 25° C. and 24 h at 85° C. The resulting 2-methylaziridine-modified chitosan oligosaccharides (COS) were precipitated in acetone, washed with methanol to remove excess 2-methylaziridine, and dried in vacuo.

Scheme 1 depicts chitosan oligosaccharide modification with 2-methylaziridine and subsequent functionalization with acrylates.

SCHEME 1

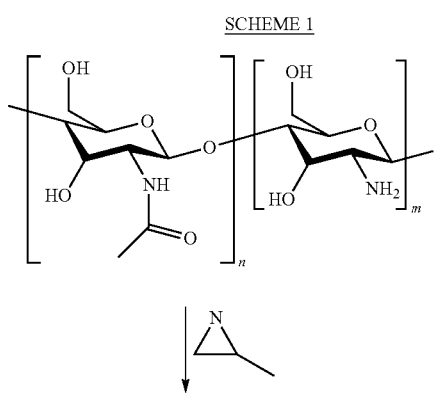
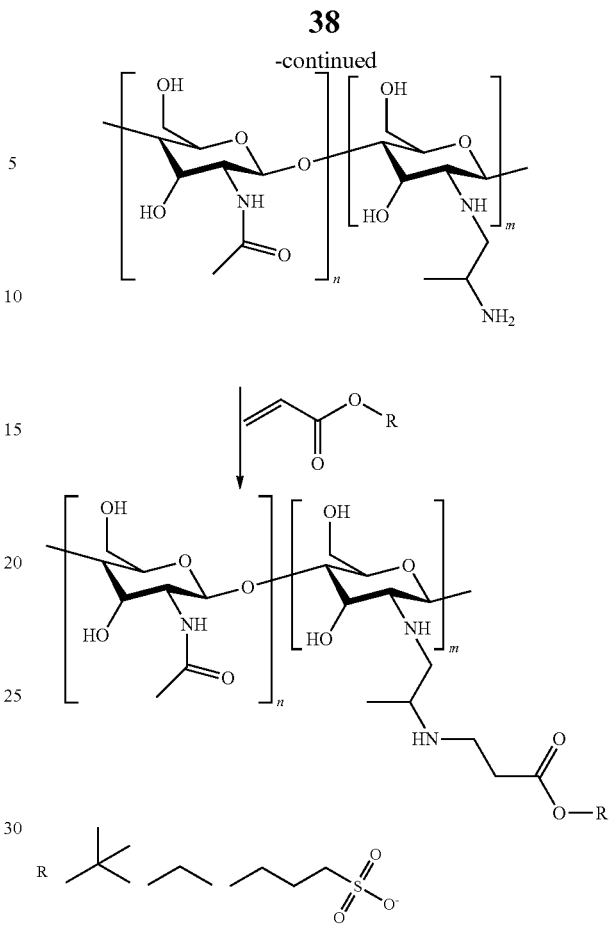

Acrylate Modifications of Chitosan Oligosaccharides

The mucoadhesive properties of COS were altered by the Michael addition of acrylates to the amino groups (Scheme 1). Ethyl acrylate (EA, 2.08 mL) and tert-butyl acrylate (TBuA, 2.78 mL) were added to COS (500 mg) in a solution of water (6.00 mL), methanol (14.00 mL), ammonium hydroxide (1.00 mL). Methanol was excluded from the reaction solvent for the addition of sulfopropyl acrylate (SPA) because the SPA is water soluble. More specifically, SPA (4.43 g) was added to COS (500 mg) in a solution of water (20.00 mL) and ammonium hydroxide (1.00 mL). A 10-fold molar excess of acrylate (vs. primary amine) was used for all reactions to maximize the acrylate addition. After 72 h stirring at room temperature, acrylate-modified COS was precipitated with acetone, collected via centrifugation, and washed with methanol to remove excess reagent. The SPA product was washed copiously with ethanol. The resulting EA-, TBuA-, and SPA-modified COS (COS-EA, COS-TBuA, and COS-SPA, respectively) were dried in vacuo overnight and stored at room temperature. Removal of unreacted acrylate from the products was verified by the disappearance of the vinyl protons in the $^1$H NMR spectra. Acrylate-modified COS was characterized by $^1$H NMR (Bruker 400 MHz DRX spectrometer) to determine the degree of substitution and product purity. Representative $^1$H NMR peaks were as follows:

COS: 1H NMR (D$_2$O, 400 MHz): δ—0.8-1.1 (br, 3H), 1.9 (s, 3H), 2.3-2.9 (br, 4H), 3.3-4.0 (br, 5H), 4.4 (s, 1H).

COS-EA: 1H NMR (D$_2$O, 400 MHz): δ—0.8-1.1 (br, 6H), 1.9 (s, 3H), 2.3-2.9 (br, 4H), 3.3-4.0 (br, 5H), 4.1 (s, 2H), 4.4 (s, 1H).

COS-TBuA: 1H NMR (D$_2$O, 400 MHz): δ—0.8-1.1 (br, 12H), 1.9 (s, 3H), 2.3-2.9 (br, 4H), 3.3-4.0 (br, 5H), 4.4 (s, 1H).

COS-SPA: 1H NMR (D$_2$O, 400 MHz): δ—0.8-1.1 (br, 6H), 1.9 (s, 3H), 2.3-2.9 (br, 4H), 3.3-4.0 (br, 5H), 4.1 (s, 2H), 4.4 (s, 1H).

Calculations used to determine the degrees of deacetylation and substitution, and FT-IR characterization data are provided in Example 12 and FIGS. 10A-D.

Synthesis of NO-Releasing Chitosan Oligosaccharides

To impart NO storage and release, N-diazeniumdiolate NO donors were formed on the secondary amines of the COS and acrylate-modified COS (Lu, Y., et al., *Biomaterials*, 35, 1716-1724 (2014)). Modified chitosan oligosaccharides (15 mg) were dissolved in a solution of water (300 μL), methanol (700 μL) and 5.4 M sodium methoxide (25 μL) in a 1 dram vial equipped with a stir bar. The open vial was placed in a 160 mL Parr general purpose stainless steel pressure vessel and stirred vigorously. Oxygen was removed from the reaction vessel by purging with argon (10 s, 8 bar) thrice, followed by three longer argon purges (10 min, 8 bar). The vessel was then filled with potassium hydroxide-purified NO gas (10 bar) for 72 h at room temperature. Afterwards, the argon purging procedure was repeated to remove unreacted NO. N-diazeniumdolate-modified chitosan oligosaccharides (COS-NO, COS-EA-NO, COS-TBuA-NO, and COS-SPA-NO) were precipitated in acetone, collected via centrifugation to yield a yellow powder, dried in vacuo, and stored at −20° C. until further study.

Chemiluminescence Detection of NO Release

A Sievers 280i Chemiluminescence Nitric Oxide Analyzer (Boulder, Colo.) was used to quantify NO release. Prior to analysis, the instrument was calibrated with air passed through a NO zero filter (0 ppm NO) and 26.8 ppm of NO standard gas (balance N$_2$). The N-diazeniumdiolate modified chitosan oligosaccharides (1.0 mg) were immersed in 30 mL of deoxygenated PBS (pH 6.5) at 37° C. whereupon released NO was carried by N$_2$ gas to the detector at a flow rate of 80 mL/min. Additional N$_2$ flow was supplied to the sample flask at 200 mL/min to match the collection rate of the instrument. Analysis was terminated once NO concentrations fell below 10 ppb NO/mg COS-NO. Additionally, a Perkin Elmer Lambda 40 UV/Vis spectrometer was used to obtain UV-Vis spectra of 0.1 mg/mL solutions of all compounds in 50 mM sodium hydroxide. This basic solution was used in order to avoid undesirable N-diazeniumdiolate NO donor degradation that begins immediately at neutral pH.

Turbidimetric Titrations of Mucins

Gastric pig mucin (960 mg) was dissolved in 250 mL of sterile phosphate buffer (PB) at 4° C. for 18 h. The mucin suspension was centrifuged (1,500×g, 4° C., 0.5 h) to remove insoluble components. The resulting mucin solution was stored in sterile containers at 4° C. for up to 1 week prior to use. Solutions of mucin and acrylate-modified chitosan oligosaccharides were prepared by combining 236 μL of the purified mucin solution with 34 μL of the chitosan oligosaccharide solutions (3.6-54.5 mg/mL in sterile PB) in a 96-well plate. The mucin and chitosan solutions were incubated for 1 h at 37° C. with gentle shaking (100 rpm) after which the absorbance was read at 540 nm using a Thermoscientific Multiskan EX plate reader. A corrected absorbance was obtained after subtracting the absorbance of the chitosan oligosaccharides (i.e., without mucin) from the COS-mucin absorbance.

Zeta Potentials of Mucin-Chitosan Oligosaccharide Aggregates

Gastric pig mucin (10.0 mg) was dissolved in 10.00 mL sterile PB at 4° C. for 18 h. The mucin suspension was centrifuged (1,500×g, 4° C., 0.5 h) to remove insoluble components. The resulting mucin solution was stored in sterile containers at 4° C. for up to 1 week prior to use. Modified chitosan oligosaccharide solids were added to the mucin solution, vortexed until dissolved, and incubated for 1 h at 37° C. Lower concentrations of mucin and chitosan oligosaccharides were used in this assay to prevent corrosion of the electrochemical cell used in zeta potential measurements. The zeta potential (i.e., surface charge) of the mucin-chitosan aggregate was determined using a Malvern Zetasizer Nano-ZS equipped with a 10 mW HeNe laser (633 nm) and a NIBS detector at an angle of 173°.

Gel Electrophoresis

Concentrated stocks of chitosan oligosaccharides (COS and COS-SPA) and NO-releasing chitosan oligosaccharides (COS-NO and COS-SPA-NO) or DTT (20 μL) were added to HBE mucus (40 μL), stirred gently, and incubated at room temperature for 2 h with gentle rocking. As CF sputum contains proteolytic enzymes, the incubation time was decreased to 1 h to reduce enzymatic degradation of the sample.

Agarose Mucin Gel Electrophoresis

Following treatment, samples were separated by electrophoresis as previously described (Ramsey, K. A., et al., Journal of Visualized Experiments, 112, e54153 (2016)). In brief, samples (40 μL) were loaded onto a 0.8 wt % agarose gel in 1×TAE buffer with 1 wt % SDS for electrophoretic mucin separation at 80 V for 90 min. The gel was subsequently reduced with 10 mM DTT for 20 min. Mucins were transferred by vacuum (45 mbar, 1.5 h) in 4×SSC buffer onto a nitrocellulose membrane with a pore size of 0.45 μm (Optitran BA-S 85 membrane, GE Healthcare Life Sciences, Piscataway, N.J.). Following blocking of nonspecific interactions with powdered milk (3 wt % in DPBS) for 1 h, mucins were detected by exposure to diluted primary antibodies raised against MUC5AC and MUC5B (0.1 μg/mL in 3% milk) overnight (3° C.). The membranes were washed thrice with DPBS (10 min) and fluorescently labeled with secondary antibodies (0.2 μg/mL in 3 wt % powdered milk, 1 h, 25° C.). The gels were subsequently washed in DPBS again and then analyzed using a LI-COR Odyssey CLx Infrared Imaging System (LI-COR Biosciences, Lincoln, Nebr.). Migration distances were quantified using Image J (National Institute of Health, Bethesda, Md.). For CF sputum samples, migration distances were normalized to the PBS-treated sample to account for the large degree of heterogeneity.

Confocal Microscopy

Prior to loading onto the agarose gel, CF sputum samples (5 μL) exposed to COS, COS-NO, COS-SPA, or COS-SPA-NO were carefully smeared on glass microscopy slides to prevent mechanical disruption of mucin and DNA network. The samples were fixed with NBF (10 vol %), washed with DPBS, and blocked with BSA (3 wt % in DPBS) for 1 h at room temperature. Mucin networks were visualized by immunohistochemical detection. First, MUC5AC and MUC5B were identified via exposure to primary antibody solutions (0.4 and 0.2 μg/mL for mouse anti-MUC5AC and rabbit anti-MUC5B, respectively). The slides were washed with DPBS three times (10 min) prior to exposure to secondary antibodies (1 μg/mL Alexa 488 and 594 anti-rabbit and mouse, respectively) and DAPI (5 μg/mL) for 1 h at 25° C. to facilitate quantitative measurement. The slides were then washed with DPBS (10 min) and mounted with Fluorsave (Calbiochem). Confocal images were obtained with an Olympus FV 1000 (Olympus, Hamilton, Bermuda) using a 20× objective.

Parallel Plate Rheology

Spontaneously expectorated sputum from one CF patient collected at a single time point was used for rheological measurements. Concentrated solutions of COS-NO (27.8 µL) were added to 250 µL aliquots of sputum to achieve final COS-NO concentrations of 0, 5, 10, and 20 mg/mL. Sputum samples were slowly rotated at room temperature for 1 h. The rheological properties of the treated samples were measured via amplitude sweep experiments over a stress range of 0.025-50 Pa at a single frequency (1 Hz) on a Bohlin Gemini Rheometer (Malvern Instruments, Worcestershire, UK) with a 20 mm diameter parallel plate set to a gap thickness of 50 mm. Rheological measurements were performed at 23° C. to minimize sample dehydration. The elastic modulus (G') and viscous modulus (G") were determined from the linear regimes as previously reported (Seagrave, J., et al., *Respiratory Research* 2012, 13, 98). All values are reported as the mean±standard error of the mean (SEM) for a minimum of three separately evaluated aliquots of the treated sputum sample.

Statistical Analysis

All values are reported as the mean±standard deviation for three or more pooled experiments unless otherwise noted. Statistical significance was determined using the two-tailed student's t-test.

Deacetylation and Degree of Substitution Calculations

Calculation of Degree of Deacetylation

Calculation of degree of deacetylation of chitosan oligosaccharides following degradation in hydrogen peroxide was determined according from the following equation adapted from Ishii (Ishii, D., et al., *Green Chemistry*, 16 (4), 1764-1767 (2014)).

$$\text{Degree Deacetylation} = \left(1 - \frac{I_{methyl}/3}{I_{H2-H6}}\right) \times 100$$

Where $I_{methyl}$ indicates the protons from the acetylated unit (2.3 ppm) and $I_{H2-H6}$ (3.5-4.4) are protons found on both the acetylated and deacetylated units. Following degradation, the chitosan oligosaccharides were 75% deacetylated.

Calculation of % Modification of Primary Amines of COS-EA $$\frac{I_{OCH2CH3}/I_{OCH(CHNH2)O}}{DD} \times 100$$

Where $I_{OCH2CH3}$ is a singlet at 4.1 ppm representing the ethyl acrylate modification, $I_{OCH(CHNH2)O}$ is the proton found on the backbone of all monomers (s, 4.4 ppm), and DD is the degree of deacetylation (0.75). This calculation was adapted from Sashiwa (Sashiwa, H., et al., *Carbohydrate Research*, 338 (6), 557-561 (2003)).

Calculation of % Modification of Primary Amines of COS-TBuA $$\frac{I_{OCC3H9}/I_{OCH(CHNH2)O}}{DD} \times 100$$

Where $I_{OCC3H9}$ is a broad peak at 1.3 ppm indicating the tert-butyl acrylate modification, $I_{OCH(CHNH2)O}$ is the proton found on the backbone of all monomers, and DD is the degree of deacetylation (0.75). This calculation was adapted from Sashiwa.

Calculation of % Modification of Primary Amines of COS-SPA $$\frac{I_{OCH2CH2CH2SO3}/I_{OCH(CHNH2)O}}{DD} \times 100$$

Where $I_{OCH2CH2CH2SO3}$ is a singlet at 4.4 ppm indicating the sulfopropyl acrylate modification, $I_{OCH(CHNH2)O}$ is the proton found on the backbone of all monomers, and DD is the degree of deacetylation (0.75). This calculation was adapted from Sashiwa.

UV-VIS Analysis

Spectra of modified chitosan oligosaccharides solutions (0.1 mg/mL, PBS pH 6.5) were obtained using a Perkin Elmer Lambda 40 UV/Vis spectrometer. Exposure to NO gas resulted in the formation of N-diazeniumdiolates as indicated by absorbance maxima at 253 nm (Hrabie, J. A. and Keefer, L. K., *Chemical Reviews*, 102 (4), 1135-1154 (2002)).

Absorbance peaks at 350 nm, which indicate nitrosamine formations (Wang, P. G., et al., *Chemical Reviews*, 102 (4), 1091-1134 (2002)) were not detected. The results are shown in FIGS. 9A-9D.

Turbidity of GPM and Chitosan Oligosaccharides in Phosphate Buffered Saline

To determine the effect of electrostatic on the mucoadhesion of chitosan oligosaccharides, turbidity measurements were compared in phosphate buffer (pH 6.5) and phosphate buffered saline (pH 6.5). With the exception of the addition of 140 mM sodium chloride (NaCl) to the phosphate buffer, the assay was performed as described above. The addition of sodium chloride in the phosphate buffered saline minimized the electrostatic interactions between the oligosaccharides and mucins. For all of the modified chitosan oligosaccharides, except COS-SPA, the addition of NaCl reduced the ability of the chitosan oligosaccharide to aggregate mucin. This reduced ability to aggregate mucin is monitored by decreased turbidity. Of note, at concentrations above 4.5 mg/mL, decreases in turbidity due to disaggregation of chitosan-mucin complexes were observed for COS and COS-TBuA. This disaggregation at high concentrations is characteristic of mucoadhesive polymers (Sogias, I. A., et al., *Biomacromolecules*, 9 (7), 1837-1842 (2008)). The results are shown in FIGS. 12A-12D.

Results

NO-Releasing Mucoadhesive Chitosan Oligosaccharides

The mucoadhesive nature of chitosan is believed to be derived from electrostatic and hydrophobic interactions, as well as hydrogen bonding between chitosan and mucins. Of these interactions, electrostatic attractions between the positively charged primary amine on chitosan and the negatively charged sialic acid and ester sulfate groups on mucins predominate (Sogias, I. A., et al., *Biomacromolecules*, 9, 1837-1842 (2008)). Sogias and Mencchicchi have demonstrated that blocking the primary amines on chitosan with acetyl groups (i.e., decreasing the deacetylation of the chitosan) reduces its ability to bind and aggregate mucin in solution. (Sogias, I. A., et al, *Biomacromolecules*, 9, 1837-1842 (2008); Menchicchi, B., et al., *Biomacromolecules*, 15, 3550-3558 (2014)).

To determine how chitosan mucoadhesion effects NO delivery and efficacy, three structurally distinct acrylate modifications were used to sterically block the primary amines on 2-methylaziridine-modified chitosan oligosaccharides (COS) (Scheme 1). Acrylates were chosen as the route to modification because propenoates covalently bind to chitosan under mild synthetic conditions. Specific acrylate modifications were also selected based on their commercial availability. Ethyl acrylate and tert-butyl acrylate were compared to determine if increasing the steric bulk from an ethyl group to a tert-butyl group altered the mucoadhesive nature of COS. To reduce mucoadhesion, a negatively charged acrylate (sulfopropyl acrylate) was employed to electrostatically repel mucus, in addition to sterically hinder the primary amine.

Reaction conditions for the Michael addition of acrylates to the COS scaffold were varied to influence modification efficiency. All reactions were carried out at room temperature as heating to 50° C. produced side-reactions between ethyl acrylate and the chitosan backbone. The primary amine on COS ($RNH_3^+$, pKa~10) is deprotonated in basic solution (pH 12), thereby increasing reactivity towards the β-carbon of the acrylate vinyl group. In this manner, the modification of COS with TBuA is improved from 11±1% at pH 7 (i.e., neutral conditions) to 83±15% at pH 12. These reaction conditions resulted in similar modification improvements (~80-98%) for all three acrylates (Table 1). Differences between modification efficiencies for the three acrylates were not significant as determined by one-way ANOVA ($F_{(2,10)}$=1.42, p=0.31).

kinetics of acrylate-modified chitosan oligosaccharides are generally more influenced by the hydrophobicity of the chitosan backbone rather than the exterior functional groups.

The formation of the N-diazeniumdiolate NO donor was characterized using UV-Vis spectroscopy. For all compounds, UV-Vis spectra showed an absorbance maximum at 253 nm following exposure to high pressures of NO gas, confirming N-diazeniumdiolate NO donor formation (Hrabie, J. A. and Keefer, L. K. *Chemical Reviews*, 102, 1135-1154 (2002)). Absorbance peaks at or near 350 nm were not observed, indicating little or no formation of potentially carcinogenic nitrosamines (Wang, P. G., et al., *Chemical Reviews*, 102, 1091-1134 (2002)). The absorbance spectra for each of the modified chitosan oligosaccharides are provided herein.

Mucoadhesion of Acrylate- and 2-Methylaziridine-Modified Chitosan Oligosaccharides Turbidimetric titrations of gastric pig mucin (GPM) with acrylate-modified COS were performed to determine the mucoadhesive properties of the chitosan oligosaccharide scaffolds. In the presence of low concentrations of mucoadhesive polymers, mucins form light scattering self-assembled complexes (Sogias, I. A., et al., *Biomacromolecules*, 9, 1837-1842 (2008); Rossi, S., et al., *European Journal of Pharmaceutical Sciences*, 10, 251-257 (2000)). As such, the turbidity of mucin solutions (as measured by corrected absorbance) is expected to increase with the addition of mucoadhesive scaffolds, resulting in increased absorbance measurements. At larger concentrations, mucoadhesive polymers have been shown to disaggregate

TABLE 1

Acrylate modification efficiency and NO-release characteristics of chitosan oligosaccharides in PBS (pH 6.5, 37° C.).[a]

|  | Degree of Substitution[b] (%) | $[NO]_{total}$[c] (µmol/mg) | $[NO]_{max}$[d] (ppb/mg) | $t_{(1/2)}$[e] (min) | $t_d$[f] (h) |
|---|---|---|---|---|---|
| COS | — | 0.44 ± 0.11 | 2800 ± 600 | 36.1 ± 2.8 | 7.85 ± 0.75 |
| COS-EA | 86 ± 4 | 0.42 ± 0.16 | 3200 ± 1100 | 28.8 ± 5.2 | 7.62 ± 0.67 |
| COS-TBuA | 83 ± 15 | 0.42 ± 0.09 | 2500 ± 400 | 25.3 ± 8.6 | 7.74 ± 0.74 |
| COS-SPA | 98 ± 15 | 0.39 ± 0.12 | 3300 ± 1100 | 28.9 ± 4.3 | 6.72 ± 1.92 |

[a]All values are reported as the mean ± standard deviation for 3 or more pooled experiments.
[b]Relative to primary amines,
[c]Total NO,
[d]Max NO Flux,
[e]Half-life,
[f]Duration of NO-release To impart NO storage and release, N-diazeniumdiolate NO donors were formed at the secondary amine sites on the modified chitosan oligosaccharides via exposure to high pressures of NO gas (Lu, Y., et al., *Biomaterials*, 35, 1716-1724 (2014)). Nitric oxide storage was tuned by maintaining constant solvent ratios (3:7 water:methanol) and base concentrations for all scaffolds, resulting in similar NO payloads ($[NO]_{total}$~0.4 µmol/mg) and release kinetics ($t_{1/2}$~30 min) for both the unmodified COS and acrylate-modified scaffolds (Table 1). While NO release from N-diazeniumdiolates may be altered by charge stabilization or hydrophobicity imparted from local functional groups (Riccio, D. A. and Schoenfisch, M. H. *Chemical Society Reviews*, 41, 3731-3741 (2012)), the acrylate modifications did not significantly alter the hydrophobicity of the materials and provided comparable NO-release kinetics. Without being bound by theory, it is believed that the similar NO-release half-lives exhibited herein indicates the NO-release mucin-polymer complexes (Sogias, I. A., et al., *Biomacromolecules*, 9, 1837-1842 (2008)). Alternately, the turbidity (i.e., absorbance) of mucin solutions should remain constant in the presence of muco-inert scaffolds. Turbidity was monitored at 540 nm to maximize sensitivity towards GPM-chitosan complexes while minimizing the absorbance of free chitosan oligosaccharides in solution ($\lambda_{max}$=375 nm).

The turbidity of GPM solutions increased rapidly (nearly 4-fold) at low concentrations (≤3 mg/mL) of the COS, COS-EA, and COS-TBuA scaffolds, indicating significant mucoadhesion with mucins in solution (FIG. 1). At concentrations ≥4.5 mg/mL, disaggregation of chitosan mucin complexes was observed for COS and COS-TBuA. The addition of COS-SPA to GPM solutions resulted in a slight increase in the turbidity of the solutions at high concentrations. As electrostatic interactions between the positively charged chitosan and negatively charged mucins facilitate mucoadhesion (Menchicchi, B., et al., *Biomacromolecule*, 15, 3550-3558 (2014); Sogias, I. A., et al., *Biomacromolecules*, 9, 1837-1842 (2008); Khutoryanskiy, V. V. *Macromolecular Bioscience*, 11, 748-764 (2011)), the corresponding electrostatic repulsion between the mucins and negatively charged sulfonate group of COS-SPA likely circumvented the formation of chitosan-mucin aggregates at low concentrations. At larger concentrations (>3 mg COS-SPA/mL), small increases in turbidity were observed and attributed to the attractive forces (e.g. hydrophobic or hydrogen bonding) between the chitosan oligosaccharide backbone and mucin particles (Sogias, I. A., et al., *Biomacromolecules*, 9, 1837-1842 (2008)).

While the TBuA and EA modifications were expected to sterically block the mucoadhesive primary amines on the COS scaffold, any steric hindrance did not significantly alter the mucoadhesion compared to the unmodified COS scaffold. Without being bound by theory, it is believed that the retained mucoadhesive properties are the result of insufficient steric blocking of the positively charged amine or hydrophobic interactions between the modified group and the mucins. To determine the extent of mucoadhesion due to electrostatics, the turbidity assay was repeated in PBS. The addition of sodium chloride to the solution minimizes electrostatic interactions between chitosan and mucins (Sogias, I. A., et al., *Biomacromolecules*, 9, 1837-1842 (2008)). For all modified chitosan oligosaccharides, the addition of sodium chloride reduced the turbidity of the solutions, indicating that electrostatic attraction between the chitosan oligosaccharides and mucins was retained, even after the chitosan was modified to prevent interactions between the positively charged amine and negatively charged groups on the mucins.

Figure 2:
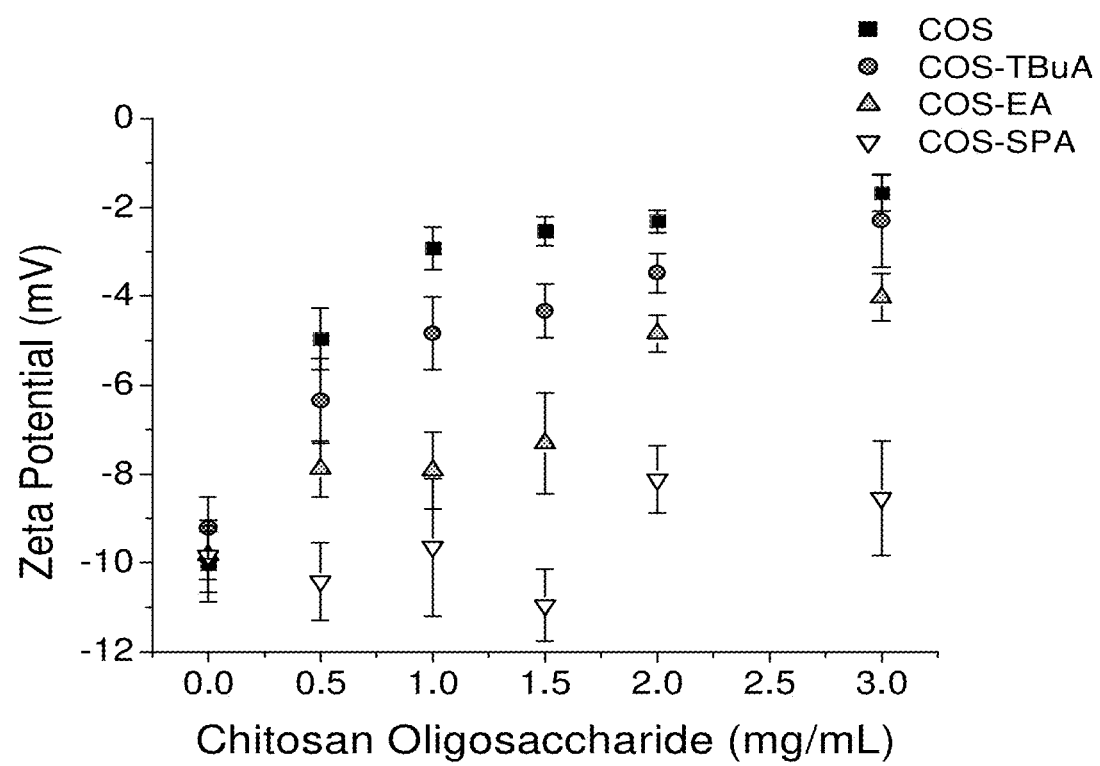
FIG. 2 shows the Zeta potential measurements of gastric pig mucin (GPM)-chitosan aggregates formed upon the addition of chitosan oligosaccharides to mucin solutions (1 mg/mL in 10 mM PB, pH 6.5).

Zeta potential measurements of chitosan-mucin aggregates corroborated the turbidimetric titration results (FIG. 2). At pH 6.5, blank GPM solutions exhibited a zeta potential of −9.8±0.5 mV. Adding chitosan oligosaccharides modified with neutral functional groups (COS, COS-TBuA, and COS-EA) to dilute mucin solutions resulted in increased zeta potentials. Treatment of GPM solutions with negatively charged COS-SPA did not alter the measured zeta potential at concentration tested, further demonstrating the reduced mucoadhesive properties of COS-SPA.

Electrophoretic Separation of Purified Mucus Following Treatment with Chitosan Oligosaccharides To determine the effects of NO on mucin size (i.e., molecular weight), mucus collected from CF HBE cultures was separated by agarose gel electrophoresis following treatment with increasing concentrations of control chitosan scaffolds (i.e., non-NO-releasing) and NO-releasing chitosan oligosaccharides. The mucolytic action of the NO-releasing chitosan oligosaccharides was evaluated using both MUC5B and MUC5AC, the key mucins responsible for gel formation in the airway. The concentrations of these mucins are known to increase during pulmonary exacerbations in CF (Henke, M. O., et al., *American Journal of Respiratory and Critical Care Medicine*, 175, 816-821 (2007)). Strongly and weakly mucoadhesive chitosan oligosaccharides (COS and COS-SPA, respectively) were used to evaluate the effects of scaffold mucoadhesion on mucin migration. Any increase in the mucin migration distance after exposure to chitosan oligosaccharides reflects a change in size and/or charge of the mucin multimers, showing a beneficial therapeutic effect in the treatment of CF mucus.

Figure 3:
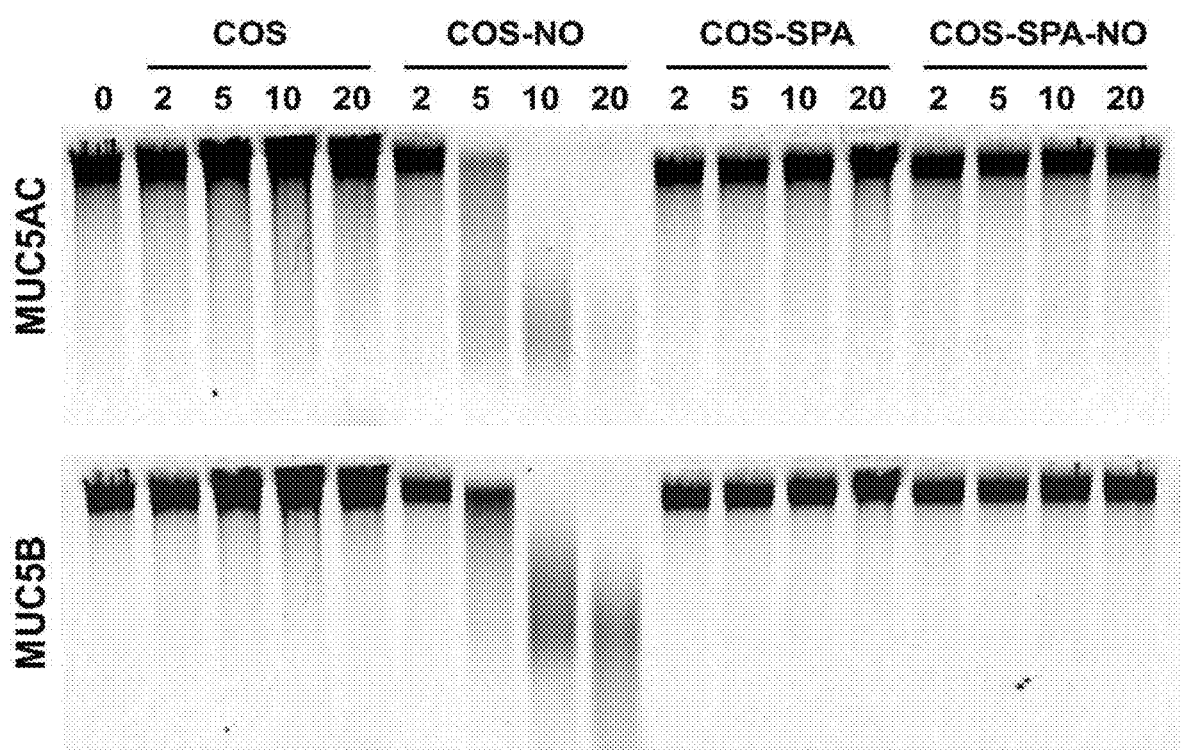
FIG. 3 is a representative Western blot of MUC5AC and MUC5B mucins from HBE culture washings from a donor with cystic fibrosis treated with COS, COS-NO, COS-SPA, and COS-SPA-NO for 2 h at 25° C. with concentrations ranging from 0-20 mg/mL.
Figure 4A:
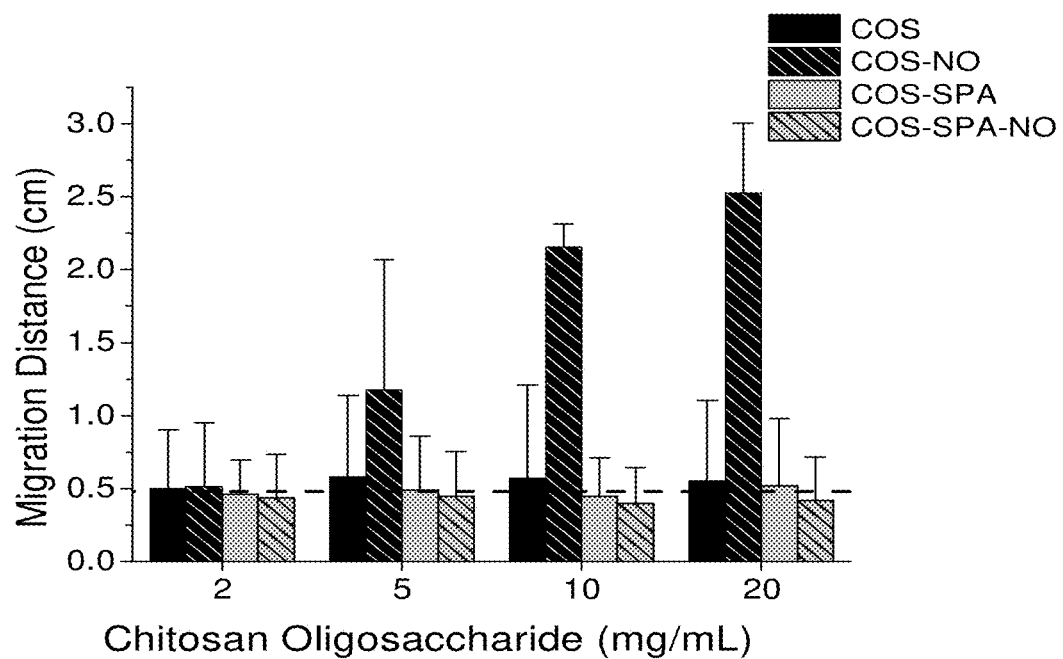
FIGS. 4A and 4B depict the migration distances of (FIG. 4A) MUC5AC and (FIG. 4B) MUC5B mucins from CF-HBE culture washings following treatment with modified chitosan oligosaccharides for 1 h at room temperature. The migration distances of mucin treated with an equal volume of PBS are denoted with dashed horizontal lines. All values are presented as the mean±standard deviation for 3 or more pooled experiments. Asterisks (*) indicate significant differences (p<0.05) relative to treatment with PBS (0 mg/mL).
Figure 4B:
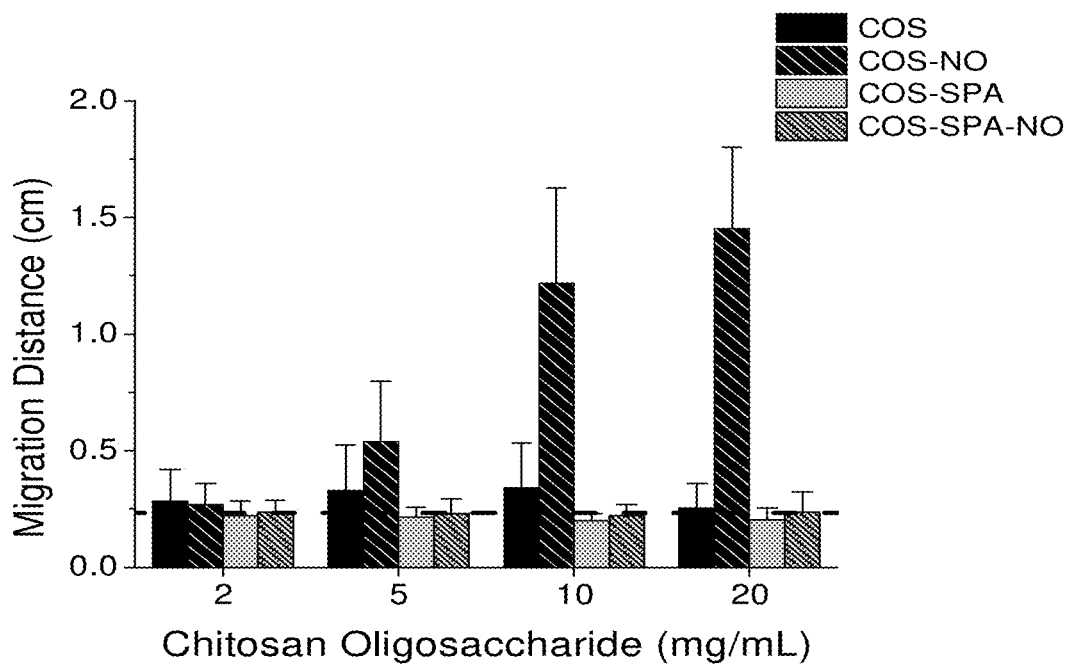

Compared to treatment with blank PBS, mucin migration was not affected by exposure to control COS and COS-SPA scaffolds regardless of the scaffold's mucoadhesive properties (FIG. 3). Treatment with the weakly mucoadhesive NO-releasing COS-SPA (COS-SPA-NO) scaffold similarly had no impact on mucin migration. However, treatment with the strongly mucoadhesive COS-NO increased the migration distances of both MUC5AC and MUC5B mucins relative to controls (p≤0.05) in a dose-dependent manner at 10 mg/mL (FIGS. 4A and 4B). The increase in mucin migration may be attributed to the pharmacological effects of NO, since treatment with the control scaffold alone did not affect migration. In this manner, the reduced size of the mucin multimers leads to faster migration. Without being bound by theory, it is believed scaffold mucoadhesion is necessary for effective NO delivery as treatment with COS-SPA-NO did not alter the migration of MUC5AC or MUC5B. Also, the poor scaffold-mucin association with negatively charged COS-SPA does not facilitate localized NO release, thereby requiring greater doses for equivalent therapeutic activity. Similar observations for bacteria and NO-releasing silica and dendrimer macromolecular scaffolds have been reported (Carpenter, A. W. and Schoenfisch, M. H. *Chemical Society Reviews*, 41, 3742-3752 (2012)). Indeed, the association of dendrimers (Lu, Y., et al., *Biomacromolecules*, 14, 3589-3598 (2013); Sun, B., et al., *Biomacromolecules*, 13, 3343-3354 (2012); Worley, B. V., et al., *Molecular Pharmaceutics*, 12, 1573-1583 (2015)) and silica (Hetrick, E. M., et al., *ACS Nano*, 2, 235-246 (2008); Carpenter, A. W., et al., *ACS Nano*, 5, 7235-7244 (2011); Slomberg, D. L., et al., *ACS Applied Materials & Interfaces*, 5, 9322-9329 (2013); Carpenter, A. W., et al., *Biomacromolecules*, 13, 3334-3342 (2012)) with bacteria (membranes) improve the antimicrobial action of NO release as a result of more targeted and localized NO delivery. The design of mucoadhesive NO-releasing scaffolds would be advantageous for ensuring target proximity and increased therapeutic action.

Figure 5:
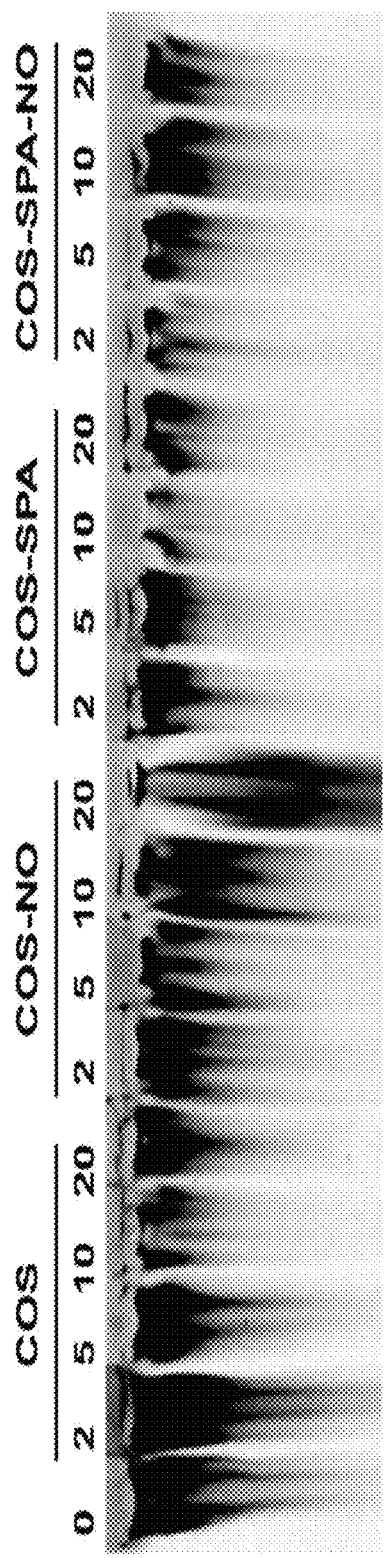
FIG. 5 is a representative Western blot of MUC5AC mucins from CF sputum treated with COS, COS-NO, COS-SPA, and COS-SPA-NO for 1 h at 25° C. with concentrations ranging from 0-20 mg/mL. Similar trends were observed for MUC5B.
Figure 6A:
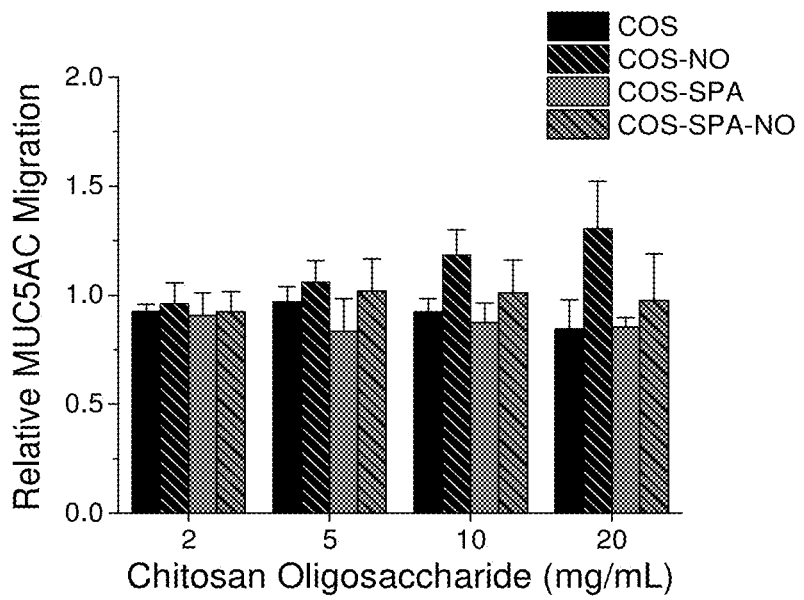
FIGS. 6A and 6B depict the relative migration distances of (FIG. 6A) MUC5AC and (FIG. 6B) MUC5B mucins from CF sputum following treatment with modified chitosan oligosaccharides for 1 h at room temperature. Migration distances were normalized to CF sputum samples treated with an equal volume of PBS. All values are presented as the mean±standard deviation for n=3 or more pooled experiments.
Figure 6B:
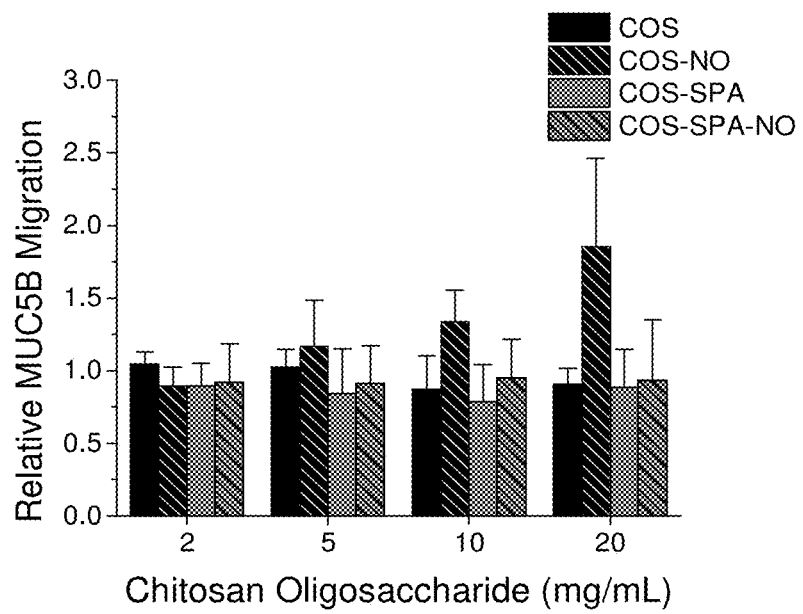

Electrophoretic Separation of CF Sputum Following Treatment with Chitosan Oligosaccharides While NO released from COS-NO increased the migration of polymeric mucins, the complexity of CF sputum (e.g., high concentrations of DNA, bacteria, inflammatory proteins and cells) may influence NO delivery and potency. The effects of COS, COS-NO, COS-SPA, and COS-SPA-NO on mucins in CF sputum were evaluated via agarose gel electrophoresis. As with HBE mucus, treatment with control (non-NO-releasing) chitosan scaffolds or COS-SPA-NO did not affect mucin migration (FIG. 5). In contrast, mucin migration was increased following treatment of MUC5AC and MUC5B mucins with COS-NO at concentrations ≥10 mg/mL (FIGS. 6A and 6B), further supporting mucolytic activity of NO for this NO-release scaffold. Of note, the concentration of chitosan oligosaccharides used in this assay is higher than the concentration used in the turbidity assay. The concentration of mucins is also higher in sputum (approximately 6.5 mg/mL) (Henderson, A. G., et al., *Journal of Clinical Investigation*, 124, 3047-3060 (2014)) than mucin concentration used in the turbidity assay (3.0 mg/m); indicating that the ratio of chitosan to mucin (mg/mg) is similar in both assays. It is proposed by Klinger-Strobel that muco-inert scaffolds are more effective for drug delivery in CF airways due to improved mucus penetration (Klinger-Strobel, M., et al., *Expert Opinion on Drug Delivery*, 1-24 (2015)). However, the pharmacological target of many such drugs lies beyond the mucus layer whereas COS-NO targets the accumulated, adherent mucus itself. Indeed, the mucolytic activity of NO-releasing chitosan oligosaccharides appeared to be dependent upon the mucoadhesive properties of the COS scaffold for both HBE mucus and CF sputum, with the weakly mucoadhesive COS-SPA-NO scaffold demonstrating no beneficial therapeutic effect.

Fluorescent Microscopy of CF Sputum

To visualize NO-mediated changes in the network formed by mucins and DNA in CF sputum, treated samples were imaged with a confocal laser scanning microscope. In the PBS-treated samples (FIGS. 7A-7D), networks of MUC5AC (red) and MUC5B (green) were intertwined, forming three-dimensional architectures characterized by thick mucin filaments (FIG. 7A, white arrows) and web-like mucin sheets. As detected by intense DAPI (blue) staining, intact neutrophils were also embedded within the three-dimensional mucin network. The level of extracellular DNA throughout the sputum samples (FIGS. 7F, 7J, 7N, and 7R) was enhanced upon treatment with COS or COS-SPA chitosan oligosaccharides, the result of enhanced neutrophil and inflammatory cell death (Dou, J., et al., *Carbohydrate Polymers*, 75, 119-124 (2009)). Treatment with COS-SPA and COS-SPA-NO had no other discernable effects on the CF sputum architecture.

Figures 7A, 7T:
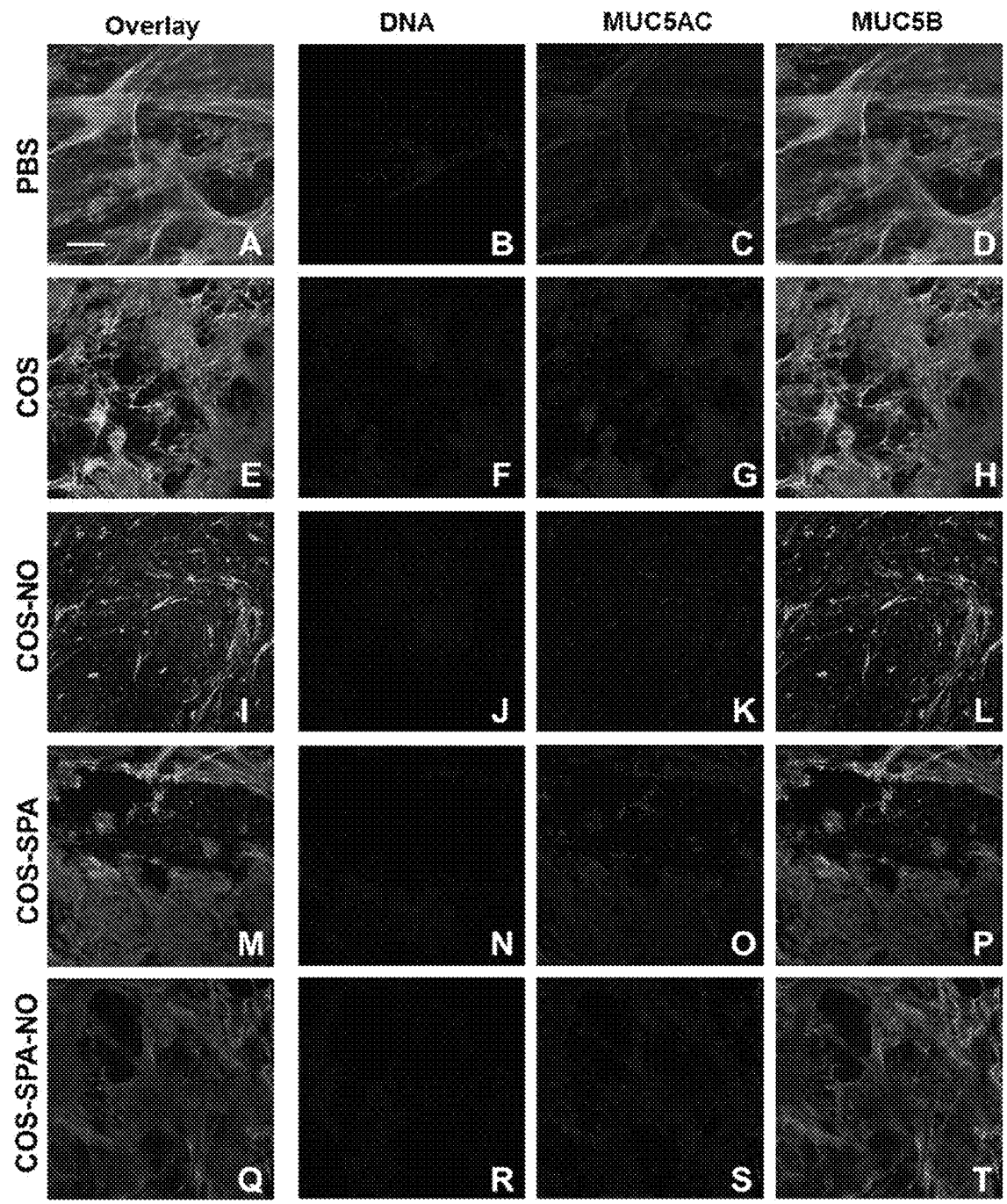
FIGS. 7A-7T show confocal microscopy images of CF sputum treated with PBS (FIGS. 7A-7D) or 20 mg/mL COS (FIGS. 7E-7H), COS-NO (FIG. 7I-7L), COS-SPA (FIGS. 7M-7P), or COS-SPA-NO (FIGS. 7Q-7T) for 1 h at 25° C. Arrows indicate long strands of mucins in untreated samples (FIG. 7A) which aggregate and form clumps upon treatment with COS (FIG. 7E).

The positively charged chitosan variants, COS and COS-NO, altered the appearance of the mucin networks in CF sputum. The COS control alone induced mucin clustering as evidenced by both signal intensification and size reduction of the mucin sheets (FIG. 7E, white arrows), indicating that the COS-mucin electrostatic interactions persisted in the complex viscoelastic environment of CF sputum. Nitric oxide-release via COS-NO further degraded the mucin network, as depicted by a lower overall mucin signal and relaxed mucin network (FIGS. 7K-7L). Samples treated with COS-NO (FIGS. 7K-7L) lacked the long filaments of mucin that were abundant in the PBS-treated samples (FIG. 7A, white arrows). These microscopic observations suggest intense disruption of the mucin network by COS-NO. The NO-mediated mucin disentanglement reduces sputum elasticity since high mucin entanglement correlates with elevated sputum elasticity (Hassett, D. J., et al., *Adv. Drug Delivery Rev.*, 54, 1425-1443 (2002)).

Treatment with COS-SPA-NO did not alter the sputum network (FIGS. 7Q-7T). Without being bound by theory, it is believed that electrostatic repulsion between the chitosan oligosaccharide backbone and negatively charged mucins prevents effective chitosan oligosaccharide penetration into the most dense mucin matrix. In this manner, the NO release from COS-SPA-NO is ineffective at altering the mucin network.

CF Sputum Rheology

Mucolytics are designed to decrease the biophysical properties of mucus, thereby increasing mucociliary clearance and pulmonary function (Henderson, A. G., et al., *Journal of Clinical Investigation*, 124, 3047-3060 (2014); Anderson, W. H., et al., *American journal of respiratory and critical care medicine*, 192, 182-190 (2015)).

Figure 8A:
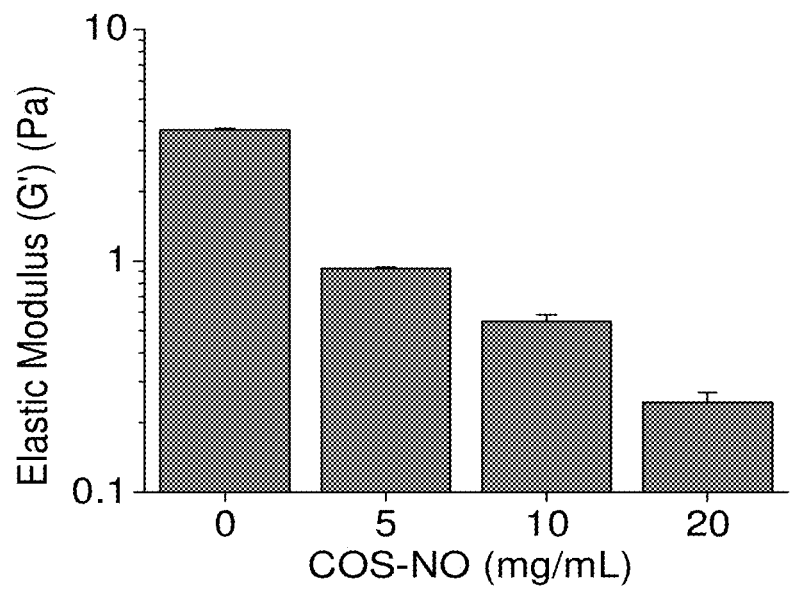
FIGS. 8A and 8B show the (FIG. 8A) elastic and (FIG. 8B) viscous moduli of CF sputum following treatment with COS-NO for 1 h at 25° C. Values presented as the mean±standard error of the mean for n=3 triplicate measurements. Asterisks (*) indicate significant differences (p<0.05) relative to treatment with PBS (0 mg/mL).
Figure 8B:
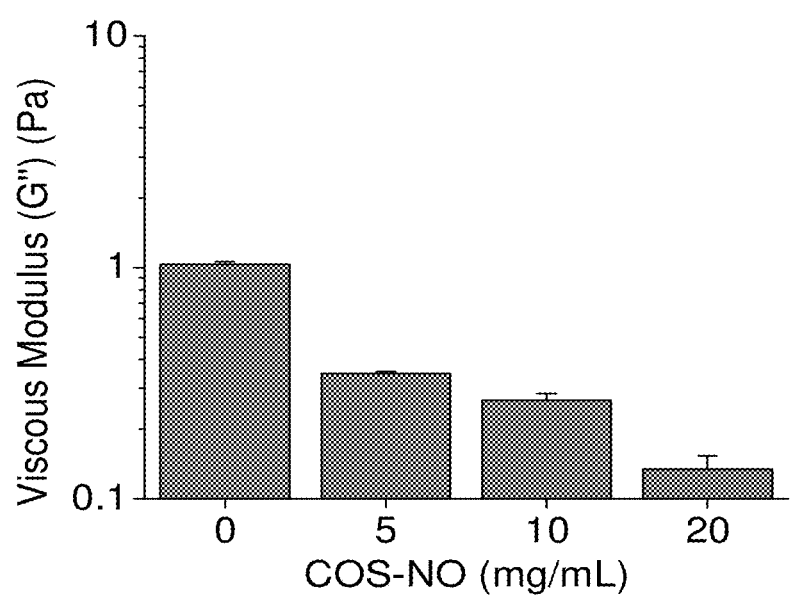
Figures 9A, 9B, 9C, 9D:
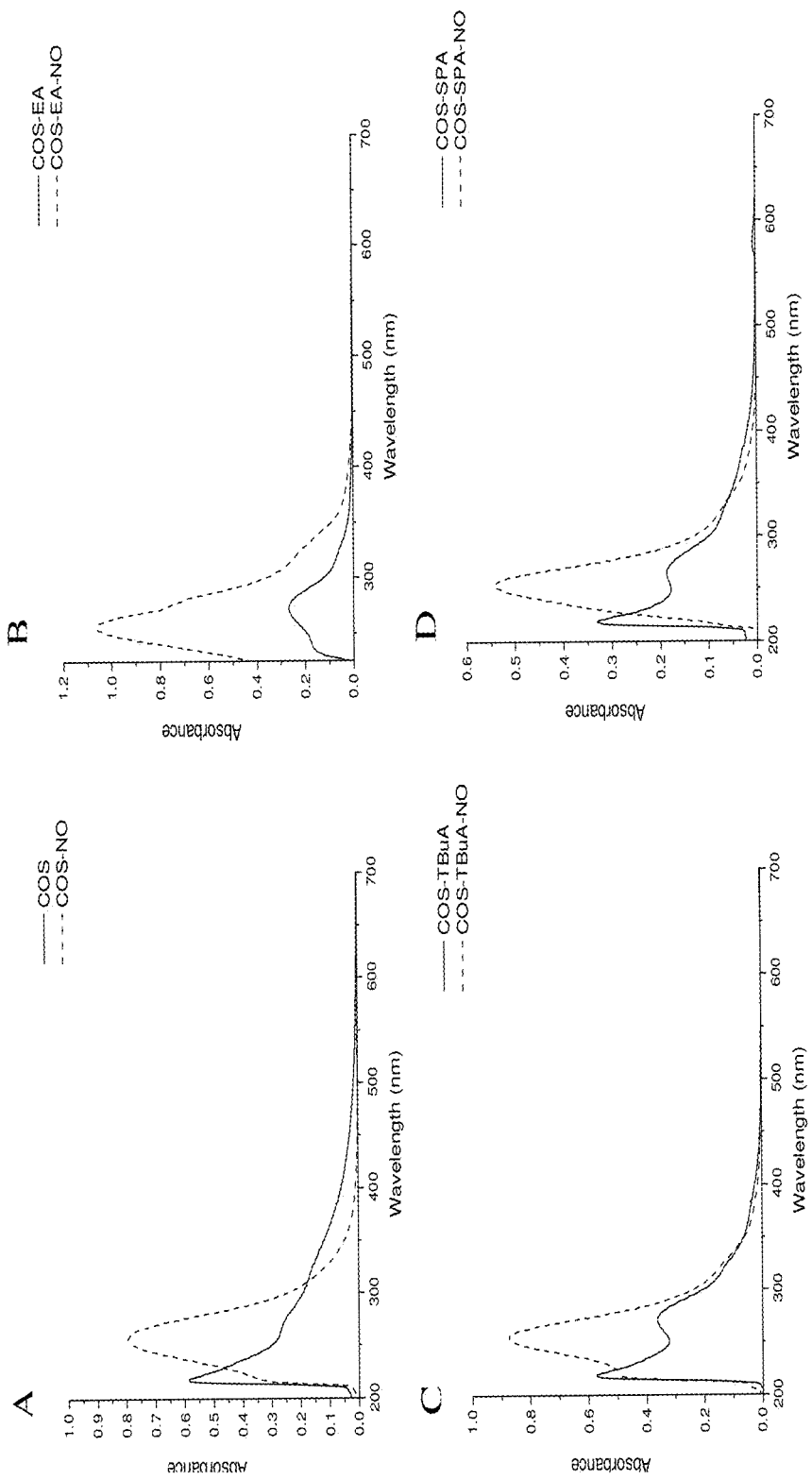
FIGS. 9A-9D depict UV Vis Spectra of (FIG. 9A) COS, (FIG. 9B) COS-EA, (FIG. 9C) COS-TBuA, and (FIG. 9D) COS-SPA before and after N-diazeniumdiolate formation by exposure to high pressures of NO gas.
Figures 10A, 10B, 10C, 10D:
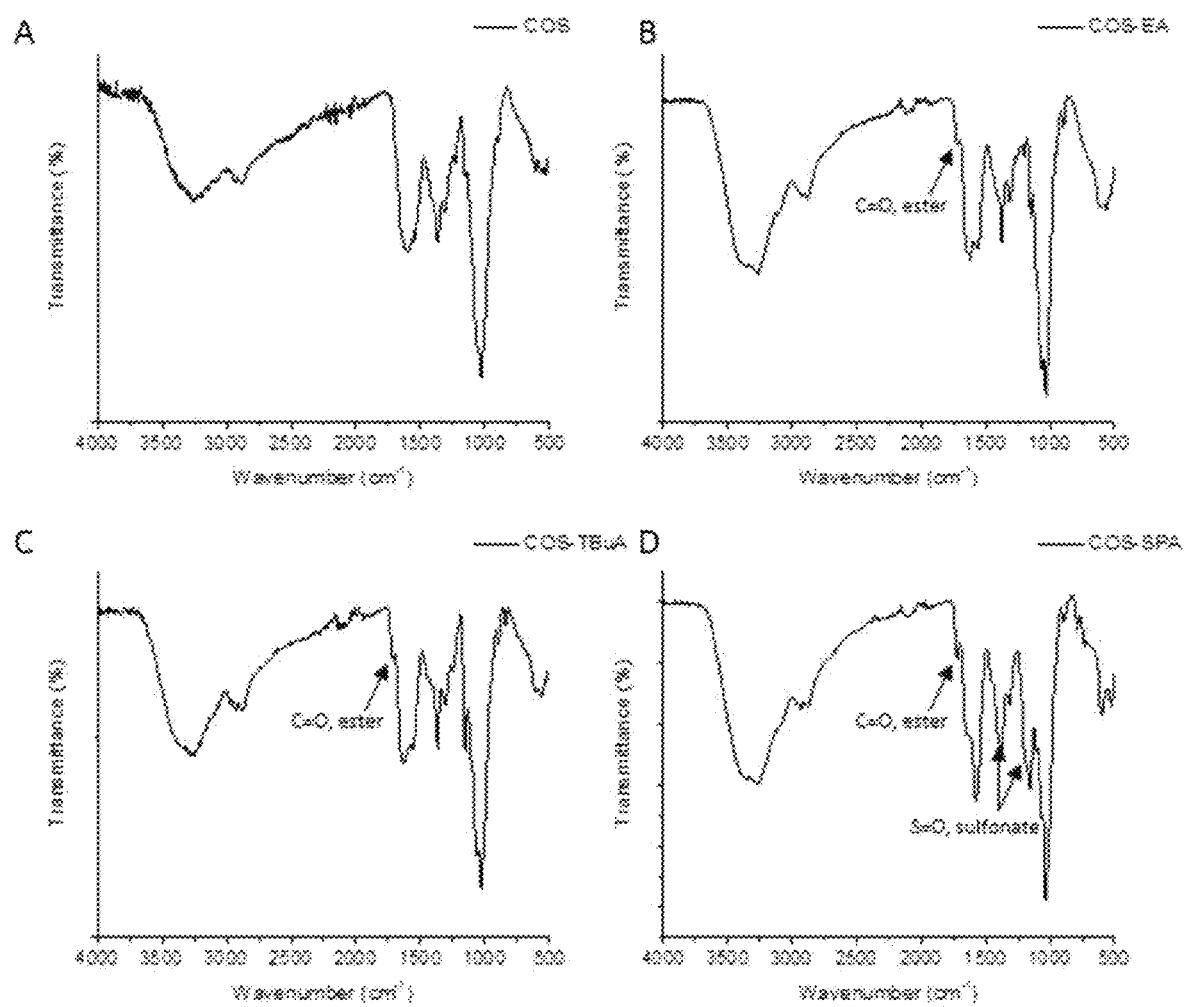
FIGS. 10A-10D depict the FT-IR spectra of modified chitosan oligosaccharides. The spectra of the modified chitosan oligosaccharides were taken with FT-IR to further characterize the successful addition of the acrylate groups to the COS backbone for (FIG. 10A) COS, (FIG. 10B) COS-EA, (FIG. 10C) COS-TBuA, and (FIG. 10D) COS-SPA.
Figure 11:
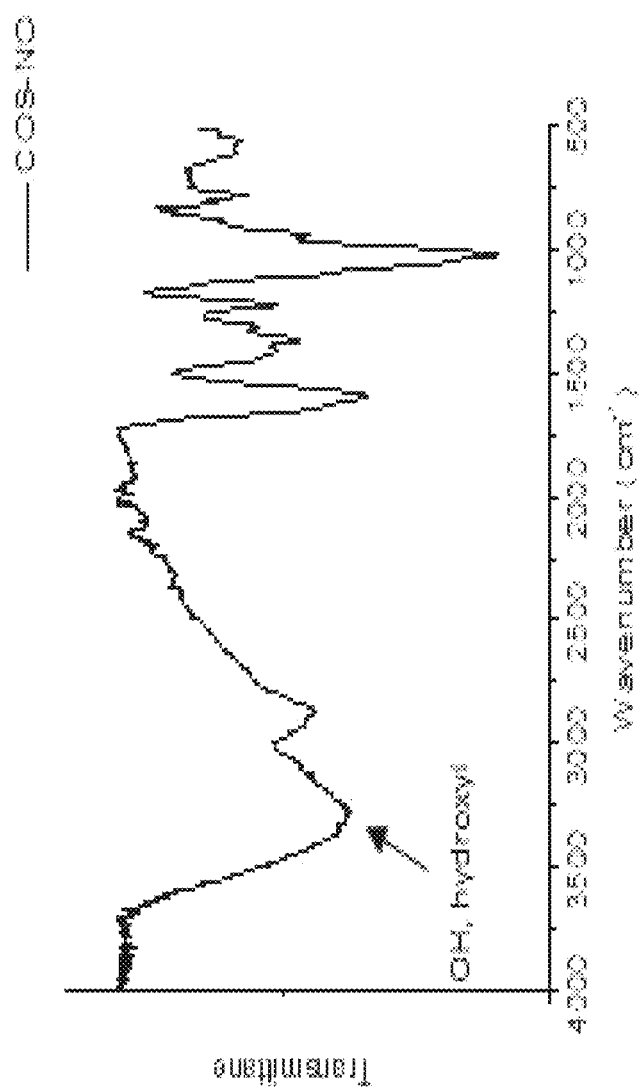
FIG. 11 shows the FT-IR spectra for COS-NO which illustrates that the hydroxyl groups of the chitosan backbone are retained after N-diazeniumdiolate formation.
Figures 12A, 12B, 12C, 12D:
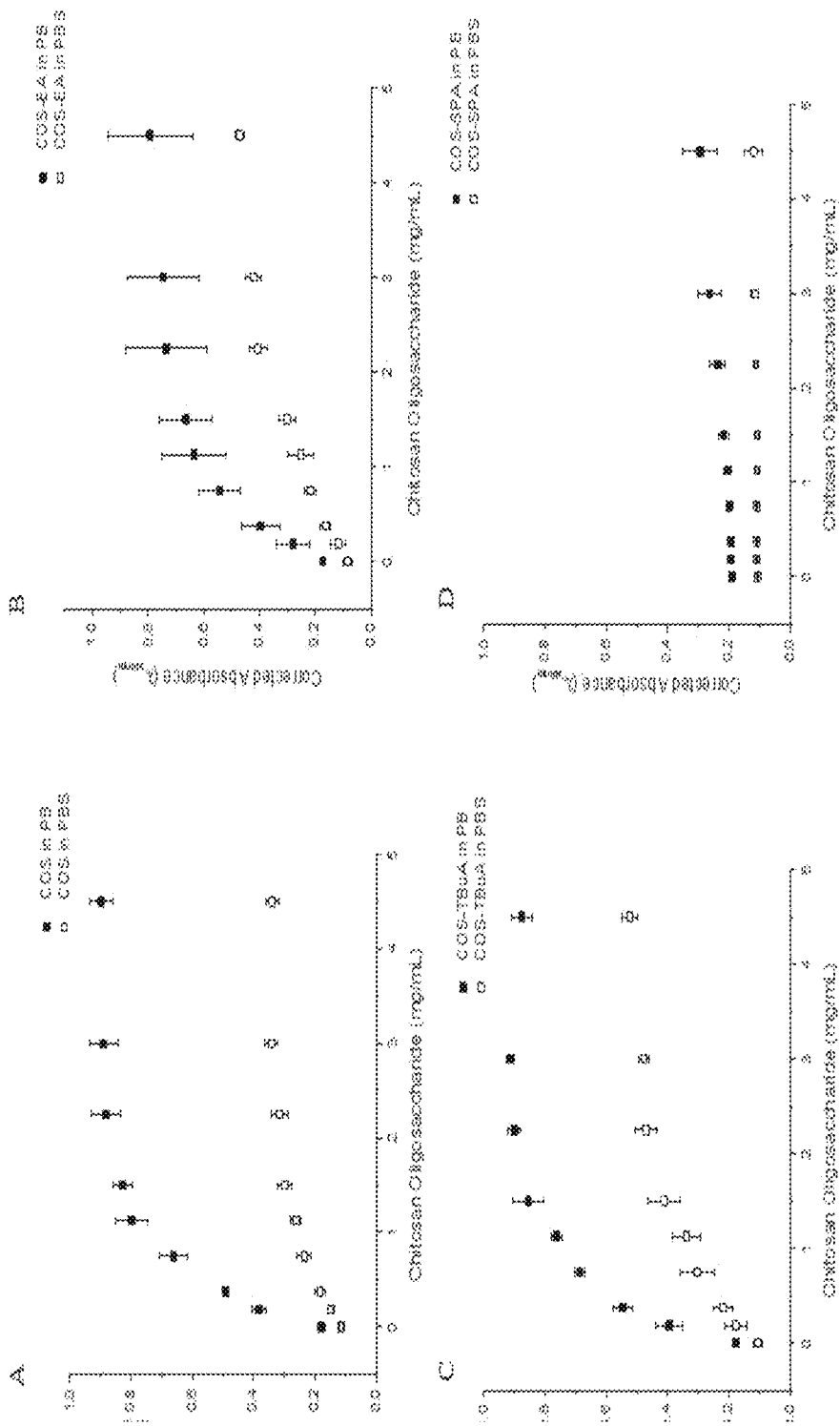
FIGS. 12A-12D show the turbidimetric titrations of (FIG. 12A) COS, (FIG. 12B) COS-EA, (FIG. 12C) COS-TBuA, and (FIG. 12D) COS-SPA in phosphate buffer (pH 6.5) and phosphate buffered saline (pH 6.5, 140 mM NaCl).

As reported herein, parallel plate rheology was used to measure both the elastic (G') and viscous (G") moduli, and evaluate how treatment with COS-NO affected the biophysical properties of CF sputum. After treatment with COS-NO for 1 h at room temperature, dose-dependent reductions in CF sputum viscosity and elasticity were observed relative to controls (FIGS. 8A and 8B). At the lowest concentration tested (5 mg/mL), COS-NO reduced sputum elasticity and viscosity by 74.9±0.4 and 66.3±1.2%, respectively, compared to PBS-treated blanks. Treatment of the CF sputum with a 4× concentration of COS-NO (20 mg/mL) reduced the sputum elasticity and viscosity by 93.4±0.7 and 87.0±2.0%, respectively. These results indicate that COS-NO is highly effective at decreasing the viscoelastic properties of CF sputum at short (1 h) exposure periods.

While it is difficult to compare rheological data in the literature due to widely varying exposure and measurement parameters (Lai, S. K., et al., *Adv. Drug Delivery Rev*, 61, 86-100 (2009)), as disclosed herein, the polyglucosamines provide substantial and beneficial changes in sputum viscoelasticity comparable to conventional mucolytic therapies used to treat CF (e.g., N-acetylcysteine, dornase alfa), while additionally providing anti-microbial activity, in particular, against *mycobacterium*. With conventional treatment, Seagrave reported that N-acetylcysteine treatment (30 µM) for 24 h decreased the viscosity and elasticity of HBE mucus by an order of magnitude versus controls (Seagrave, J., et al., *Respiratory Research*, 13, 98 (2012)). Shah observed reduced expectorated sputum viscosity and elasticity (59 and 68%, respectively) in patients with CF following treatment with dornase alfa for 10 d (2.5 mg, twice daily) (Shah, P. L., et al., *Thorax*, 51, 119-125 (1996)). Only slightly greater concentrations of COS-NO (an exemplified polyglucosamine) were required to similarly alter sputum rheological properties relative to the N-acetylcysteine and dornase alfa used previously; however, longer exposure times and/or greater NO payloads decrease the required therapeutic dose for equivalent action. Demonstrated herein is a shorter therapeutic exposure compared to previous reports (1 h compared to 24 h) (Seagrave, J., et al., *Respiratory Research*, 13, 98 (2012)) or 10 daily treatments (Shah, P. L., et al., *Thorax*, 51, 119-125 (1996)) and achieved similar reductions in CF sputum viscosity and elasticity, demonstrating the utility of COS-NO as a potential mucolytic agent.

The diminished elastic and viscous moduli of CF sputum may be attributed to alterations in the DNA network via NO-mediated DNA cleavage (Tamir, S., et al., *Chemical Research in Toxicology*, 9, 821-827 (1996); Burney, S., et al., *Mutation Research/Fundamental and Molecular Mechanisms of Mutagenesis*, 424, 37-49 (1999); Duan, J. and Kasper, D. L. *Glycobiology*, 21, 401-409 (2011)). The electrophoretic separation and confocal microscopy results indicate that NO actively alters the mucin network. As NO may be genotoxic (Felley-Bosco, E. Cancer and Metastasis Reviews, 17, 25-37 (1998)), the cyto- and genotoxicity of the materials disclosed herein should be characterized prior to preclinical or clinical studies.

Example 2

Anti-Microbial Efficacy Data

In vitro testing of COS-NO against a number of pathogens is depicted in Tables 2 and 3. The values listed for MIC and MBC in Table 2 are the concentrations of COS-NO.

TABLE 2

Broad spectrum susceptibility against nine key pathogens identified by the FDA as serious public health threat.

| Organism | Strain | Source | MIC (mg/ml) | MBC (mg/ml) |
|---|---|---|---|---|
| *Staphylococcus Aureus* (MRSA) | 328 | ATTC 33591 | 0.8 | 12.5 |
| *Staphylococcus Aureus* (MSSA) | Wichita | ATTC 29213 | 3.1 | 12.5 |

TABLE 2-continued

Broad spectrum susceptibility against nine key pathogens identified by the FDA as serious public health threat.

| Organism | Strain | Source | MIC (mg/ml) | MBC (mg/ml) |
|---|---|---|---|---|
| Pseudomonas Aeruginosa | Boston 41501 | ATCC 27853 | 0.4 | 1.6 |
| Burkholderia Cepacia | UCB 717 | ATCC 25416 | 0.2 | 0.4 |
| Mycobacterium Avium | MAC 101 | ATCC 700898 | NR | 0.4 |
| Mycobacterium Abscessus | L948 | ATCC 19977 | 6.25 | 12.5 |
| Mycobacterium Intracelullare | TMC1463 | ATCC 35767 | NR | 12.5 |
| Achromobacter Xylosoxidans | HR 01-22 | UAB | 0.8 | 3.1 |
| Stenotrophomonas Maltophilia | HR01-03 | UAB | 0.4 | 3.1 |

NR = Not Readable

American Type Culture Collection (ATTC)

University of Alabama (UAB)

MIC = Minimum Inhibition Concentration and MBC = Minimum Bactericidal Concentration for at least 3 log reduction (>99.9%) killing The values listed for MIC and MBC in Table 3 are the concentrations of NO released over time by COS-NO and are the sum of NO released during the course of the experiment. As one of skill in the art would understand NO is dynamic, so the amount of NO varies over time.

TABLE 3

Broad spectrum susceptibility against nine key pathogens identified by the FDA as serious public health threat

| Organism | Strain | Source | MIC (μmol/ml) | MBC (μmol/ml) |
|---|---|---|---|---|
| Staphylococcus Aureus (MRSA) | 328 | ATTC 33591 | 0.27 | 4.25 |
| Staphylococcus Aureus (MSSA) | Wichita | ATTC 29213 | 1.05 | 4.25 |
| Pseudomonas Aeruginosa | Boston 41501 | ATCC 27853 | 0.14 | 0.54 |
| Burkholderia Cepacia | UCB 717 | ATCC 25416 | 0.07 | 0.14 |
| Mycobacterium Avium | MAC 101 | ATCC 700898 | NR | 0.14 |
| Mycobacterium Abscessus | L948 | ATCC 19977 | 2.12 | 4.25 |
| Mycobacterium Intracelullare | TMC1463 | ATCC 35767 | NR | 4.25 |
| Achromobacter Xylosoxidans | HR 01-22 | UAB | 0.27 | 1.05 |
| Stenotrophomonas Maltophilia | HR01-03 | UAB | 0.14 | 1.05 |

NR = Not Readable

American Type Culture Collection (ATTC)

University of Alabama (UAB)

MIC = Minimum Inhibition Concentration and MBC = Minimum Bactericidal Concentration for at least 3 log reduction (>99.9%) killing The efficacy of COS-NO against *Pseudomonas aeruginosa* and *Staphylococcus aureus* was determined by treatment of sputum from two CF patients (labeled as AA and BB samples) and counting the resultant colonies (counted as CFUs). The results are shown in Table 4.

The AA sample was contacted with COS-NO and the level of *Pseudomonas aeruginosa* was determined. The 20 mg/mL NO-releasing chitosan dose killed all bacteria in two of three AA samples (AA6 and AA10). In the other (AA4), the NO release was able to decrease bacteria counts by $10^5$ CFUs. The larger concentrations resulted in no counts of *Pseudomonas aeruginosa* in all three samples.

The BB sample was contacted with COS-NO and the level of *Staphylococcus aureus* was determined. All *Staphylococcus aureus* was killed at 20 mg/mL and greater concentrations.

TABLE 4

Antibacterial efficacy against *Pseudomonas Aeruginosa* and *Staphylococcus Aureus*

| Pseudomonas count (CFU/mL sputum) | | Staphylococcus count (CFU/mL sputum) | |
|---|---|---|---|
| Sample | CFU | Sample | CFU |
| Untreated samples | | | |
| AA1 | 1.45E+08 | BB1 | 3.50E+03 |
| AA5 | 1.77E+08 | | |
| AA9 | 1.91E+08 | | |
| Treatment with NO-releasing chitosan (20 mg/mL) | | | |
| AA4 | 2.10E+03 | BB2 | ND |
| AA6 | ND | | |
| AA10 | ND | | |

TABLE 4-continued

Antibacterial efficacy against *Pseudomonas Aeruginosa* and *Staphylococcus Aureus*

| *Pseudomonas* count (CFU/mL sputum) | | *Staphylococcus* count (CFU/mL sputum) | |
|---|---|---|---|
| Sample | CFU | Sample | CFU |
| Treatment with NO-releasing chitosan (40 mg/mL) | | | |
| AA3 | ND | | |
| AA8 | ND | | |
| AA11 | ND | | |
| Treatment with NO-releasing chitosan (60 mg/mL) | | | |
| AA2 | ND | BB3 | ND |
| AA7 | ND | | |
| AA12 | ND | | |

ND = Not detected
CFU = Colony Forming Unit

Table 5 shows antimicrobial data for additional pathogens. The New Delhi Metallo-β-Lactamase (NDM-1) and *Klebsiella pneumoniae* Carbapenemase (KPC) strain isolates carry bla NDM-1 and KPC genes conferring resistance to carbapenem (CR) antibiotics. Each strain demonstrates multidrug-resistance to as many as 36 representative antibiotics in variety of drug classes.

TABLE 5

Antimicrobial activity of COS-NO.

| Organism | Resistance | Source | MIC (μmol/ml) | MBC (μmol/ml) | Notes |
|---|---|---|---|---|---|
| *Klebsiella pneumoniae* | NDM-1 | ATCC BAA-2146 | 0.43 | 1.7 | |
| Methicillin-Resistant *Staphylococcus Aureus* (MRSA) | | ATCC 33591 | 0.27 | 4.25 | |
| *Klebsiella pneumoniae* | KPC | AR-BANK#0097 | 0.85 | 1.7 | |
| *Klebsiella pneumoniae* | TEM-1, SHV-11, CTX-M15 | AR-BANK#0109 | 0.85 | 1.7 | Colistin resistant strain |
| *Pseudomonas Aeruginosa* | KPC | AR-BANK#0231 | 0.43 | 0.85 | Tobramycin resistant strain |
| *Pseudomonas Aeruginosa* | NDM-1 | AR-BANK#0246 | 0.43 | 0.85 | Tobramycin resistant strain |

Having thus described example embodiments of the present invention, it is to be understood that the invention defined by the above paragraphs is not to be limited to particular details set forth in the above description, as many apparent variations thereof are possible without departing from the spirit or scope of the present invention.

What is claimed is:

1. A method of modifying mucus in a subject in need thereof, the method comprising:
    administering a nitric oxide (NO)-releasing biopolymer to the subject, wherein the NO-releasing biopolymer is mucoadhesive and is administered to the subject in an amount that is mucolytic and antimicrobial, thereby modifying mucus in the subject, and
    wherein the NO-releasing biopolymer releases nitric oxide in an amount of about 0.1 to about 2 μmol of nitric oxide per mg of the NO-releasing biopolymer and/or has a half-life of about 15 minutes to about 24 hours, each as measured in vitro via chemiluminescence with 1.0 mg of the NO-releasing biopolymer in 30 mL of deoxygenated phosphate buffered saline (pH 7.4) at 37° C. with analysis terminated when NO concentrations are below 10 ppb NO/mg of the NO-releasing biopolymer.

2. The method of claim 1, wherein the administering comprises contacting mucus present in the subject with the NO-releasing biopolymer.

3. The method of claim 1, wherein administering the NO-releasing biopolymer results in increasing mucus clearance from the subject compared to a control.

4. The method of claim 1, wherein administering the NO-releasing biopolymer results in inhibiting or killing a pathogen in mucus present in the subject.

5. The method of claim 1, wherein the NO-releasing biopolymer is administered at a concentration that reduces the growth or kills one or more pathogens selected from the group consisting of *Staphylococcus aureus, Pseudomonas aeruginosa, Burkholderia cepacia, Achromobacter xylosoxidans, Stenotrophomonas maltophillia, Klebsiella pneumoniae, Mycobacterium avium, Mycobacterium abscessus,* and *Mycobacterium intracelullare.*

6. The method of claim 1, wherein administering the NO-releasing biopolymer results in decreasing mucus viscosity and/or elasticity in the subject by at least 10% compared to mucus viscosity and/or elasticity in the subject prior to the administering step and/or compared to a control mucus viscosity and/or elasticity.

7. The method of claim 1, wherein administering the NO-releasing biopolymer results in the NO-releasing biopolymer degrading at least a portion of mucus present in the subject.

8. The method of claim 1, wherein administering the NO-releasing biopolymer results in the NO-releasing biopolymer reducing mucin size and/or damaging the three-dimensional mucin network of at least a portion of mucus present in the subject.

9. The method of claim 1, wherein administering the NO-releasing biopolymer results in the NO-releasing biopolymer altering DNA present in the mucus.

10. The method of claim 1, wherein administering the NO-releasing biopolymer results in clearing from the subject mucus present in an airway, lung, bronchi, and/or trachea of the subject.

11. The method of claim 1, wherein the subject has or is suspected to have cystic fibrosis.

12. The method of claim 1, wherein the NO-releasing biopolymer releases nitric oxide for at least about 6 hours, as measured in vitro via chemiluminescence with 1.0 mg of the NO-releasing biopolymer in 30 mL of deoxygenated phosphate buffered saline (pH 7.4) at 37° C. with analysis terminated when NO concentrations are below 10 ppb NO/mg of the NO-releasing biopolymer.

13. The method of claim 1, wherein the NO-releasing biopolymer is administered as a monotherapy.

14. The method of claim 1, wherein the NO-releasing biopolymer is water soluble and/or has a molecular weight of about 10 kDa or less.

15. The method of claim 1, wherein the NO-releasing biopolymer is a NO-releasing polyglucosamine.

16. The method of claim 1, wherein the NO-releasing biopolymer comprises at least one structural unit of Formula I:

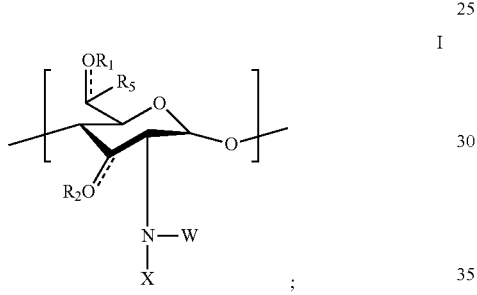

and optionally at least one structural unit of Formula II:

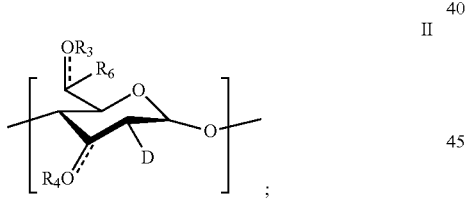

wherein,
$R_1$, $R_2$, $R_3$ and $R_4$, if present, are each independently selected from the group consisting of hydrogen, —(C=O)$C_{1-5}$ alkyl, and $C_{1-5}$ alkyl;
- - - - , in each instance, is a single or double bond, wherein in each instance where it is a double bond, $R_1$, $R_2$, $R_3$ or $R_4$ attached to the double bond-O is absent; when $R_1$ is absent, $R_5$ is hydrogen, hydroxyl, $C_{1-5}$ alkyl or $C_{1-5}$ alkoxy; when $R_3$ is absent, $R_6$ is hydrogen, hydroxyl, $C_{1-5}$ alkyl or $C_{1-5}$ alkoxy;
wherein in each instance where it is a single bond, $R_1$, $R_2$, $R_3$ or $R_4$ attached to the double bond-O is present; when $R_1$ is present, $R_5$ is hydrogen; when $R_3$ is present, $R_6$ is hydrogen;

W is -(Q-A)$_p$-B, Q-A-B, or —$C_{1-20}$ alkyl-A-B;
Q is —(CR$_c$R$_d$)$_v$—;
wherein $R_c$ and $R_d$ are, in each instance, independently hydrogen or $C_{1-5}$ alkyl; and v is an integer from 2 to 6;
p is an integer from 1 to 100;
A is

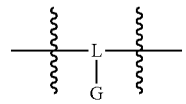

wherein, L is S, O or N; and
G, in each instance, is independently, hydrogen, or is taken together with L to form a nitric oxide donor or is absent;
X is hydrogen, $C_{1-5}$ alkyl or is taken together with N to form a nitric oxide donor;
B is absent or is selected from the group consisting of hydrogen, hydroxyl, $C_{1-5}$ alkyl, or —Y—Z, wherein Y is a spacer and Z is a polymer, terminus, or $C_{1-20}$ alkyl;
D is —NR$_a$R$_b$, wherein $R_a$ and $R_b$ are independently selected from the group consisting of hydrogen, formyl, —(C=O)$C_{1-5}$ alkyl, $C_{1-5}$ alkyl and $C_{1-5}$ alkyl ester;
or D is

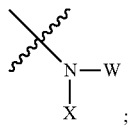

wherein the polyglucosamine comprises at least one nitric oxide donor; and
wherein G is taken together with L to form the at least one nitric oxide donor or X is taken together with N to form the at least one nitric oxide donor.

17. The method of claim 1, wherein the NO-releasing biopolymer comprises at least one nitric oxide donor that is a diazeniumdiolate.

18. A method of modifying mucus, the method comprising:
contacting a nitric oxide (NO)-releasing biopolymer to mucus, wherein the NO-releasing biopolymer is mucoadhesive and in an amount that is mucolytic and antimicrobial, thereby modifying the mucus, and
wherein the NO-releasing biopolymer releases nitric oxide in an amount of about 0.1 to about 2 µmol of nitric oxide per mg of the NO-releasing biopolymer and/or has a half-life of about 15 minutes to about 24 hours, each as measured in vitro via chemiluminescence with 1.0 mg of the NO-releasing biopolymer in 30 mL of deoxygenated phosphate buffered saline (pH 7.4) at 37° C. with analysis terminated when NO concentrations are below 10 ppb NO/mg of the NO-releasing biopolymer.

* * * * *